US012349872B2

(12) United States Patent
Sessions et al.

(10) Patent No.: US 12,349,872 B2
(45) Date of Patent: Jul. 8, 2025

(54) SAMPLE COLLECTION DEVICE AND METHOD

(71) Applicant: Ancestry.com DNA, LLC

(72) Inventors: Travis Sessions, Cedar Hills, UT (US); Aaron Devore, Lehi, UT (US); Dan H. O'Neill, Salt Lake City, UT (US)

(73) Assignee: Ancestry.com DNA, LLC, Lehi, UT (US)

( * ) Notice: Subject to any disclaimer, the term of this patent is extended or adjusted under 35 U.S.C. 154(b) by 0 days.

(21) Appl. No.: 18/139,265

(22) Filed: Apr. 25, 2023

(65) Prior Publication Data
US 2023/0285008 A1    Sep. 14, 2023

Related U.S. Application Data

(63) Continuation of application No. 16/563,800, filed on Sep. 6, 2019, now Pat. No. 11,826,027, which is a continuation of application No. PCT/US2018/022518, filed on Mar. 14, 2018.
(Continued)

(51) Int. Cl.
*B01L 3/00* (2006.01)
*A61B 10/00* (2006.01)

(52) U.S. Cl.
CPC ...... *A61B 10/0045* (2013.01); *B01L 3/50825* (2013.01); *A61B 10/0051* (2013.01);
(Continued)

(58) Field of Classification Search
CPC ............ A61B 10/0045; A61B 10/0051; B01L 3/50825; B01L 2200/16; B01L 2300/042; B01L 2300/047; B01L 2300/049
See application file for complete search history.

(56) References Cited

U.S. PATENT DOCUMENTS 2,793,776 A    5/1957  Ipari
3,477,431 A    11/1969 Walecka
(Continued)

FOREIGN PATENT DOCUMENTS

CN    205300987 U  *  6/2016  ............... G01N 1/10
EP    3235441 A1    10/2017
(Continued)

OTHER PUBLICATIONS

Ke, CN 205300987 U English Machine Translation of Abstract, Description and Claims,, 2016, obtained from wipo.int on May 9, 2024, pp. 1-4. (Year: 2016).*
(Continued)

*Primary Examiner* — Christine T Mui
(74) *Attorney, Agent, or Firm* — Fenwick & West LLP

(57) ABSTRACT

The present description relates to a sample collection device comprising a receptacle and a closure member configured to seal the receptacle. Within the closure member is provided a reservoir configured to contain a stabilization fluid capable of preserving and stabilizing a collected sample. The reservoir includes an outlet which is sealed by a sealing member. The sealing member may be openable to allow communication, or mixture, between the contents of the reservoir and the contents of the receptacle. The closure member may also include a peel foil on the end of the closure member having the outlet to ensure sterility of and to avoid tampering with the outlet and the reservoir. The method includes collecting a sample from the user using the sample collection device, mixing the sample with the stabilization fluid, and analyzing the sample thus collected.

14 Claims, 23 Drawing Sheets

Related U.S. Application Data

(60) Provisional application No. 62/471,852, filed on Mar. 15, 2017, provisional application No. 62/476,204, filed on Mar. 24, 2017.

(52) U.S. Cl.
CPC ..... *B01L 2200/16* (2013.01); *B01L 2300/042* (2013.01); *B01L 2300/047* (2013.01); *B01L 2300/049* (2013.01)

(56) References Cited

U.S. PATENT DOCUMENTS

| | | | |
|---|---|---|---|
| 3,831,742 A | 8/1974 | Gardella et al. |
| 4,131,016 A | 12/1978 | Layton |
| 4,184,483 A | 1/1980 | Greenspan |
| 4,217,798 A | 8/1980 | McCarthy et al. |
| 4,301,812 A | 11/1981 | Layton et al. |
| 4,312,950 A | 1/1982 | Snyder et al. |
| 4,409,988 A | 10/1983 | Greenspan |
| 4,449,645 A | 5/1984 | Korwin et al. |
| 4,935,342 A | 6/1990 | Seligson |
| 4,982,553 A | 1/1991 | Itoh |
| 5,283,038 A | 2/1994 | Seymour |
| 5,393,496 A | 2/1995 | Seymour |
| 5,396,986 A | 3/1995 | Fountain et al. |
| 5,714,341 A | 2/1998 | Thieme et al. |
| 5,736,322 A | 4/1998 | Goldstein |
| 5,736,355 A | 4/1998 | Dyke et al. |
| 5,830,154 A | 11/1998 | Goldstein et al. |
| 5,830,410 A | 11/1998 | Thieme et al. |
| 5,927,549 A | 7/1999 | Wood |
| 5,933,498 A | 8/1999 | Schneck et al. |
| 6,003,728 A | 12/1999 | Elliott |
| 6,048,091 A | 4/2000 | McIntyre |
| 6,152,296 A | 11/2000 | Shih |
| 6,196,979 B1 | 3/2001 | Virtanen |
| 6,228,323 B1 | 5/2001 | Asgharian et al. |
| 6,277,331 B1 | 8/2001 | Konrad |
| 6,428,962 B1 | 8/2002 | Naegele |
| 6,458,546 B1 | 10/2002 | Baker |
| D470,240 S | 2/2003 | Niedbala et al. |
| 6,543,612 B2 | 4/2003 | Lee et al. |
| 6,548,256 B2 | 4/2003 | Lienau |
| D474,280 S | 5/2003 | Niedbala et al. |
| 6,627,152 B1 | 9/2003 | Wong |
| 6,786,330 B2 | 9/2004 | Mollstam et al. |
| D507,351 S | 7/2005 | Birnboim |
| 6,939,672 B2 | 9/2005 | Lentrichia et al. |
| 6,992,182 B1 | 1/2006 | Müller et al. |
| 7,055,685 B1 | 6/2006 | Patterson et al. |
| 7,178,683 B2 | 2/2007 | Birkmayer et al. |
| 7,214,484 B2 | 5/2007 | Weber et al. |
| 7,297,485 B2 | 11/2007 | Bornarth |
| 7,303,876 B2 | 12/2007 | Greenfield |
| D574,507 S | 8/2008 | Muir et al. |
| 7,482,116 B2 | 1/2009 | Birnboim |
| 7,537,132 B2 | 5/2009 | Marple et al. |
| 7,544,468 B2 | 6/2009 | Goldstein et al. |
| 7,589,184 B2 | 9/2009 | Hogan et al. |
| 7,645,424 B2 | 1/2010 | O'Donovan |
| 7,748,550 B2 | 7/2010 | Cho |
| 7,854,104 B2 | 12/2010 | Cronin |
| 7,858,396 B2 | 12/2010 | Corstjens et al. |
| D631,350 S | 1/2011 | Beach et al. |
| D631,553 S | 1/2011 | Niedbala et al. |
| 7,866,465 B2 | 1/2011 | Dverin |
| D640,794 S | 6/2011 | Sunstrum et al. |
| D640,795 S | 6/2011 | Jackson et al. |
| 7,998,757 B2 | 8/2011 | Darrigrand et al. |
| 8,038,668 B2 | 10/2011 | Scott et al. |
| 8,062,908 B2 | 11/2011 | Mink et al. |
| 8,158,357 B2 | 4/2012 | Birnboim |
| 8,221,381 B2 | 7/2012 | Muir et al. |
| D673,265 S | 12/2012 | Nonnemacher et al. |
| 8,425,864 B2 | 4/2013 | Haywood |
| 8,431,384 B2 | 4/2013 | Hogan et al. |
| 8,470,536 B2 | 6/2013 | Birnboim |
| 8,673,239 B2 | 3/2014 | Niedbala et al. |
| 8,728,414 B2 | 5/2014 | Beach et al. |
| 9,040,675 B2 | 5/2015 | Bales et al. |
| 9,072,499 B2 | 7/2015 | Birnboim et al. |
| 9,079,181 B2 | 7/2015 | Curry et al. |
| D743,044 S | 11/2015 | Jackson et al. |
| D743,571 S | 11/2015 | Jackson et al. |
| 9,207,164 B2 | 12/2015 | Muir et al. |
| 9,410,147 B2 | 8/2016 | Gundling |
| 9,416,356 B2 | 8/2016 | Gundling |
| 9,523,115 B2 | 12/2016 | Birnboim |
| 9,757,179 B2 | 9/2017 | Formica |
| 10,000,795 B2 | 6/2018 | Birnboim et al. |
| D850,647 S | 6/2019 | Jackson et al. |
| 10,435,735 B2 | 10/2019 | Birnboim et al. |
| 10,973,497 B2 | 4/2021 | Sessions et al. |
| 2003/0089627 A1 | 5/2003 | Chelles et al. |
| 2004/0132091 A1 | 7/2004 | Ramsey et al. |
| 2006/0201948 A1 | 9/2006 | Ellson et al. |
| 2006/0252054 A1 | 11/2006 | Lin et al. |
| 2007/0170142 A1 | 7/2007 | Cho |
| 2009/0024060 A1 | 1/2009 | Darrigrand et al. |
| 2009/0216213 A1 | 8/2009 | Muir et al. |
| 2010/0021351 A1 | 1/2010 | Holländer |
| 2010/0099149 A1 | 4/2010 | Birnboim et al. |
| 2010/0258457 A1 | 10/2010 | Seelhofer |
| 2011/0020195 A1 | 1/2011 | Luotola |
| 2011/0028863 A1 | 2/2011 | Butlin et al. |
| 2011/0207621 A1 | 8/2011 | Montagu et al. |
| 2011/0212002 A1 | 9/2011 | Curry et al. |
| 2012/0024861 A1 | 2/2012 | Otsuka et al. |
| 2012/0024862 A1 | 2/2012 | Otsuka et al. |
| 2012/0046574 A1 | 2/2012 | Skakoon |
| 2012/0061392 A1 | 3/2012 | Beach et al. |
| 2012/0325721 A1 | 12/2012 | Plante et al. |
| 2013/0037427 A1 | 2/2013 | Wu |
| 2013/0092690 A1 | 4/2013 | Skakoon |
| 2013/0164738 A1 | 6/2013 | Becker |
| 2014/0005636 A1 | 1/2014 | Wang et al. |
| 2014/0120531 A1 | 5/2014 | Biadillah et al. |
| 2014/0316302 A1 | 10/2014 | Nonnemacher et al. |
| 2015/0056716 A1 | 2/2015 | Oyler et al. |
| 2017/0001191 A1 | 1/2017 | Biadillah et al. |
| 2017/0016807 A1 | 1/2017 | Biadillah et al. |
| 2017/0072393 A1 | 3/2017 | Jackson et al. |
| 2017/0130219 A1 | 5/2017 | Birnboim et al. |
| 2017/0166955 A1 | 6/2017 | Birnboim et al. |
| 2017/0226469 A1 | 8/2017 | Birnboim et al. |
| 2018/0036733 A1 | 2/2018 | Williams |
| 2019/0210778 A1 | 7/2019 | Muir et al. |
| 2019/0358628 A1 | 11/2019 | Curry et al. |

FOREIGN PATENT DOCUMENTS

| | | |
|---|---|---|
| JP | 2008-518858 A | 6/2008 |
| JP | 2010-213660 A | 9/2010 |
| JP | 2014-527615 A | 10/2014 |
| JP | 2017-194324 A | 10/2017 |
| WO | WO 1993/03167 | 2/1993 |
| WO | WO 98/03265 | 1/1998 |
| WO | WO 1998/44158 | 10/1998 |
| WO | WO 1999/39010 | 8/1999 |
| WO | WO 2007/009170 A1 | 1/2007 |
| WO | WO 2012/177656 A2 | 12/2012 |
| WO | WO 2015/017701 | 2/2015 |
| WO | WO 2016/079611 A1 | 5/2016 |
| WO | WO 2016/131859 A1 | 8/2016 |

OTHER PUBLICATIONS

European Patent Office, Extended European Search Report and Opinion, EP Patent Application No. 18768389.1, Nov. 23, 2020, eight pages.

(56) References Cited

OTHER PUBLICATIONS

European Patent Office, Extended European Search Report and Opinion, EP Patent Application No. 18864358.9, Jun. 1, 2021, eight pages.
Meulenbelt, I. et al. "High-Yield Noninvasive Human Genomic DNA Isolation Method for Genetic Studies in Geographically Dispersed Families and Populations," American Journal of Human Genetics, 1995, vol. 57, No. 1252-1254, 3 pages.
United States Office Action, U.S. Appl. No. 16/481,050, filed Nov. 2, 2020, 21 pages.
23andMe. "Providing Saliva Sample for DNA Test Kit." 23andMe: Customer Care, Oct. 24, 2019, 4 pages, [Online] [Retrieved Jun. 13, 2023], Retrieved from the Internet Archive <URL:https://web.archive.org/web/20191024001649/https:/customercare.23andme.com/hc/en-us/articles/202904530-Providing-Saliva-Sample-for-DNA-Test-Kit>.
DNAGenotek. "Collection Kits for Research." DNA Genotek Products, Mar. 14, 2018, 11 pages, [Online] [Retrieved Jun. 13, 2023], Retrieved from the Internet Archive <URL:https://web.archive.org/web/20180314033537/https:/www.dnagenotek.com/us/products/collection-human/collection-kits-for-research.html>.
The Japan Patent Office, Office Action, Japanese Patent Application No. 2020-546294, Apr. 25, 2023, eight pages.
European Patent Office, Examination Report, European Patent Application No. 18864358.9, Aug. 27, 2024, seven pages.

\* cited by examiner

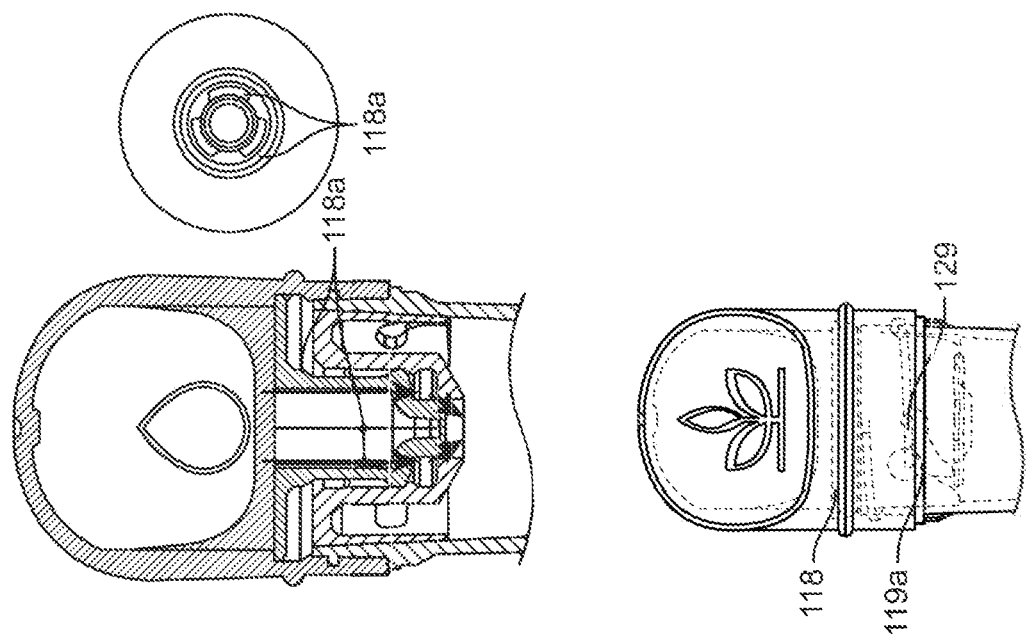
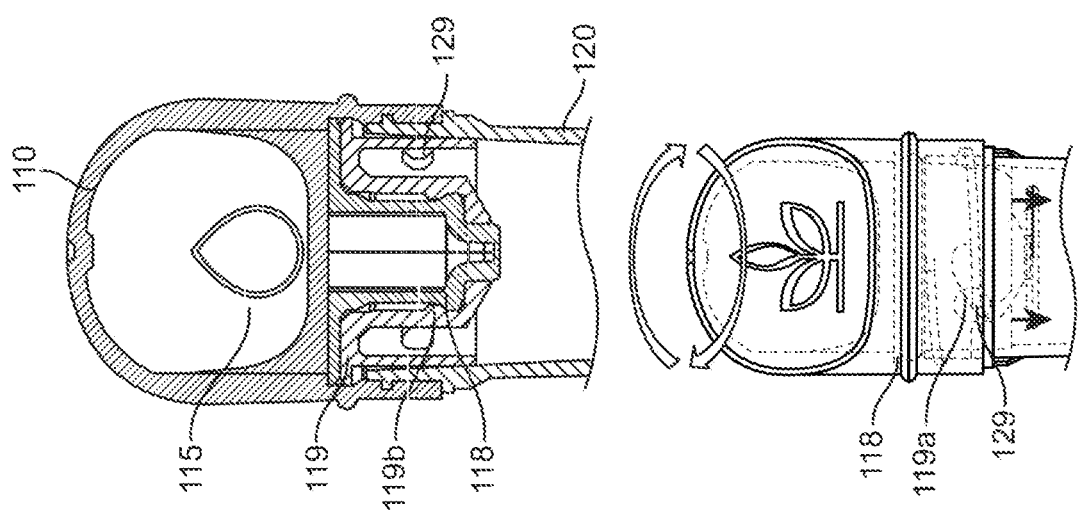
FIG. 5A

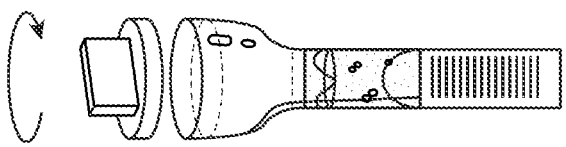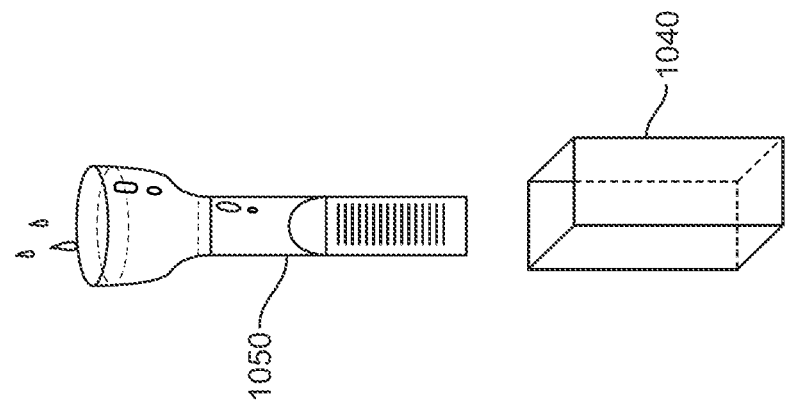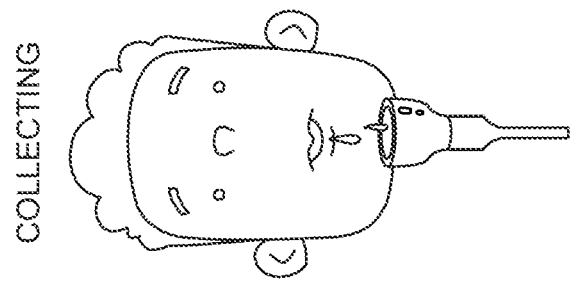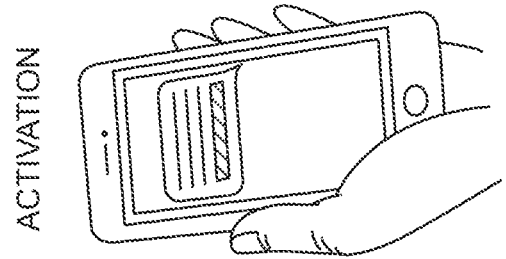
FIG. 11

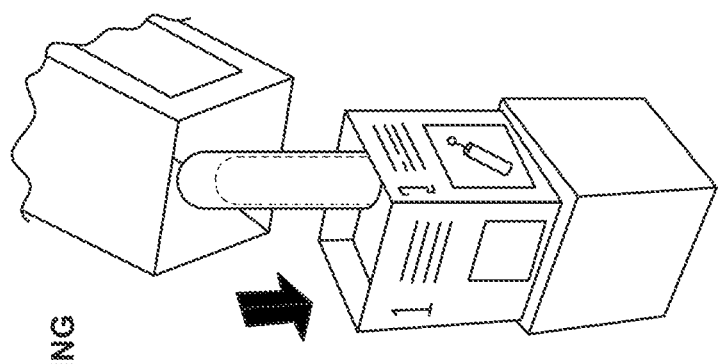
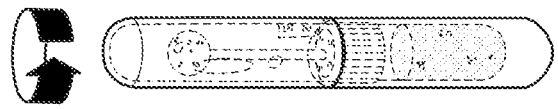
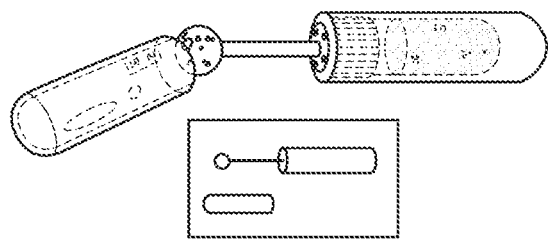
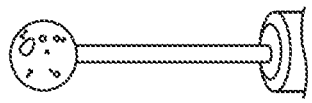
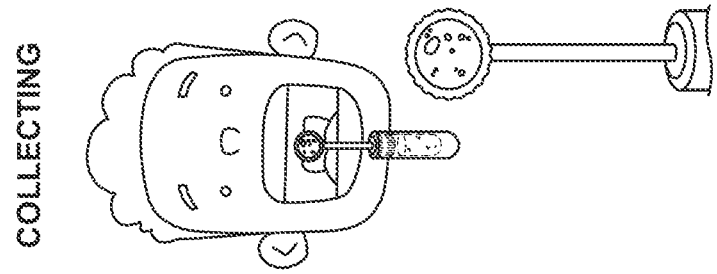
FIG. 16

SAMPLE COLLECTION DEVICE AND METHOD

CROSS REFERENCE TO RELATED APPLICATIONS

The present application is a continuation of U.S. patent application Ser. No. 16/563,800, filed Sep. 6, 2019, which is a continuation of pending International Application No. PCT/US2018/022518, filed on Mar. 14, 2018, which claims the benefit of priority to U.S. Provisional Application No. 62/471,852 filed on Mar. 15, 2017, and to U.S. Provisional Application No. 62/476,204 filed on Mar. 24, 2017, all of which are incorporated herein by reference in their entirety for all purposes.

BACKGROUND

Field of Art

The present description relates to an apparatus and method for collecting a sample and mixing the sample with a fluid. For example, a sample containing nucleic acids may be mixed with a stabilizing fluid to preserve the sample during transportation and storage.

Description of the Related Art

DNA testing is used for purposes of paternity, genealogy, disease susceptibility and forensics, etc. DNA can be extracted from virtually every type of cell in the human body. Blood samples, buccal swabs and saliva are commonly used for DNA tests. Collecting saliva is much less invasive than taking of blood and can be collected by individuals with less training than is required in the collection of blood. However, the number of cells recovered by a swabbing procedure is not large and typically less than 1-2 micrograms of DNA can be expected in the entire sample. As such, there exists the need for a collection method for obtaining a larger, more reliable sample.

Saliva is a fairly clear, colorless fluid secreted principally by the major salivary glands (parotid, submandibular, and sublingual). Its function is to lubricate and cleanse the oral cavity, as well as to initiate the process of digestion. The parotid gland primarily secretes serous (watery) saliva, while the other glands secrete a mixture of serous and mucinous (sticky) saliva. Components of saliva include albumin, globulin, mucins, and digestive enzymes.

However, once saliva has been collected, as the inside of the mouth is not a sterile source (as compared to blood), microbes can degrade the quality of the DNA after a period of time. As such, there remains a need to subsequently preserve the nucleic acids (DNA) contained in a saliva sample by contacting them with a stabilizing composition.

A variety of containers for holding diagnostic and/or nucleic acid preserving compositions and a biological sample separately in such a manner that a user may open a closure to combine the compositions and the biological sample are known. Typically, these containers are double compartment systems in which substances are stored separately and substances are combined by removal of the container closures by a user. For example, International PCT Application WO 2015/017701 describes a sample collection device having a sample tube, funnel, and cap having a capsule and a piercing insert, the capsule having a stabilization solution. After depositing the sample into the tube via the funnel, the cap is screwed onto the tube, piercing the capsule and releasing the stabilization fluid into the tube.

However, current sample collection devices can be difficult to use. Difficulties include, inter alia, awkward sizes for a typical hand, unwieldy numbers of steps for use, unclear indications of orientation of tube, instability on flat surface, caps resistant to closure; inconsistent combining of sample with stabilization composition, and non-fail safe methods for connecting a user record to a sample record. As such, there remains a need for user friendly devices to collect samples, for example, human saliva, for nucleic acid analysis or analysis of DNA for the purposes of genealogy, personalized medicine, and forensics.

SUMMARY

The present description relates to a sample collection device and a method for providing a user with the sample collection device, collecting a sample from the user, mixing the sample with a fluid, and analyzing the sample thus collected. In some embodiments, the sample may be a biological sample that degrades and therefore requires stabilization after collection of the sample, for example, during transportation and storage. For instance, the sample may be saliva or another sample containing DNA. In such embodiments, the fluid may be a stabilization fluid capable of preserving and stabilizing the DNA.

In one embodiment, the sample collection device includes a receptacle and a closure member configured to seal the receptacle. Within the closure member is provided a reservoir configured to contain a fluid, for example, a stabilization fluid. The reservoir includes an outlet which is sealed by a sealing member. The sealing member may be openable to allow communication, or mixture, between the contents of the reservoir and the contents of the receptacle. The closure member may also include a peel foil on the end of the closure member having the outlet to ensure sterility of and to avoid tampering with the outlet and the reservoir.

As described herein, the sample collection device allows for simple, user-friendly collection of a sample, such as saliva or other sample containing DNA. The sample collection device may be provided in sizes suitable for a typical hand, and the receptacle may be configured to allow easy, efficient the collection of the sample from a user. The sample collection device may also reliably preserve and/or stabilize the collected sample during transportation and storage thereof. The sample collection device can provide clear indications of orientation of the receptacle and stability of the receptacle on a flat surface. Additionally, the closure member may be configured for easy connection with the receptacle, and the sample collection device can provide consistent combining of a sample with a fluid, such as a stabilization fluid.

The method described herein relates to use of the sample collection device. The method may include the steps of: supplying a user with the sample collection device; collecting a sample from a user; transporting the sample collection device from the user's location to an analysis location; and thereafter processing and storing the sample. The user may be supplied with the sample collection device in any suitable manner, for example, by postal service or in-person in a clinical setting. The method further provides for reliably collecting a sample and preserving and/or stabilizing the sample throughout transportation, processing, and storage of the sample. This is because the method does not involve an unwieldy numbers of steps for use. And the method can provide fail safe methods for connecting a user record to a sample record. Also, the sample collection device is user-friendly and may include features to avoid contamination of the sample or tampering of the device, which provides reliable and consistent sampling.

In one embodiment, a sample collection device comprising: a receptacle having a first closed end and a second open end configured to receive a sample; and a closure member including a reservoir contained within a body of the closure member, wherein one end of the closure member is configured to seal with the second open end of the receptacle, wherein the reservoir includes a hollow body, wherein the reservoir comprises an outlet sealed with a sealing member, and wherein the sealing member is openable.

In one embodiment of the sample collection device, the reservoir further comprises a fluid contained within the hollow body of the reservoir.

In one embodiment of the sample collection device, the sample is a biological sample including nucleic acids and the fluid is a stabilization fluid capable of stabilizing nucleic acids.

In one embodiment of the sample collection device, the closure member comprises a peel foil on the end of the closure member configured to seal the second open end of the receptacle.

In one embodiment of the sample collection device, the second open end of the receptacle includes a funnel portion.

In one embodiment of the sample collection device, the sealing member comprises a one-way valve or a check valve.

In one embodiment of the sample collection device, the sealing member comprises a disc seated on the outlet and a threaded member configured to unseat the disc.

In one embodiment, the sample collection device further comprises a detachable funnel member configured to connect to the second open end of the receptacle.

In one embodiment of the sample collection device, the sealing member comprises a disc seated on the outlet, the disc including one or more channels, and the receptacle includes one or more posts formed near the second open end of the receptacle, and wherein the number of posts is equal to the number of channels, and the posts are configured to move along the channels when the closure member is connected to the receptacle.

In one embodiment of the sample collection device, the closure member comprises an outer portion configured to seal with the second open end of the receptacle and an inner portion moveable relative to the outer portion, and the sealing member comprises a disc fixed to the outer portion.

In one embodiment of the sample collection device, a compressible member is provided between at least a portion of the outer portion and the inner portion of the closure member.

In one embodiment of the sample collection device, the disc is fixed to the outer portion by way of a stem.

In one embodiment, a sample collection system comprises a sample collection device contained within a packaging, wherein the sample collection device comprises: a receptacle having a first closed end and a second open end configured to receive a sample; and a closure member including a reservoir contained within a body of the closure member, wherein one end of the closure member is configured to seal the second open end of the receptacle, wherein the reservoir includes a hollow body, wherein the reservoir comprises an outlet sealed with a sealing member, and wherein the sealing member is openable.

In one embodiment, the sample collection system further comprises a collection bag configured to seal the sample collection device within the collection bag.

In one embodiment, the sample collection system further comprises a salivation inducing composition.

In one embodiment of the sample collection system, the salivation inducing composition is chewing gum or table sugar.

In one embodiment, the sample collection system further comprises a return package, wherein the return package is configured to seal the sample collection device inside the return package.

In one embodiment of the sample collection system, the sample is a biological sample including nucleic acids and the fluid is a stabilization fluid capable of stabilizing nucleic acids.

In one embodiment, a sample collection method comprising the steps, in order, of: a depositing step of depositing a sample into a receptacle having a first closed end and a second open end; a sealing step of sealing one end of a closure member on the second open end of the receptacle, wherein the closure member includes a reservoir contained within a body of the closure member, the reservoir contains a fluid, and the reservoir includes an outlet sealed by a sealing member; and a releasing step of opening the sealing member and releasing the fluid from the reservoir into the receptacle.

In one embodiment of the sample collection method, the closure member comprises a peel foil on the end of the closure member configured to seal the second open end of the receptacle, and the method further comprises a peeling step prior to the sealing step wherein the peel foil is removed from the closure member.

In one embodiment, the sample collection method further comprises a shaking step after the releasing step wherein the sealed receptacle and closure member are agitated to mix the sample and the fluid.

In one embodiment of the sample collection method, the sealing member comprises a first layer and a second layer, each of the first layer and the second layer including a respective opening, and at least one of the first layer or the second layer is moveable relative to the other of the first layer or the second layer so as to align the respective openings, thereby opening the sealing member during the releasing step.

In one embodiment of the sample collection method, the sealing member comprises a disc seated on the outlet and a threaded member configured to unseat the disc during the releasing step.

In one embodiment of the sample collection method, the sample is a biological sample including nucleic acids and the fluid is a stabilization fluid capable of stabilizing nucleic acids.

In one embodiment of the sample collection method, the sealing member comprises a disc seated on the outlet, the disc including one or more channels, and the receptacle includes one or more posts formed near the second open end of the receptacle, wherein the number of posts is equal to the number of channels, and wherein, during the releasing step, the posts move along the channels thereby actuating the disc to unseat the disc.

In one embodiment of the sample collection method, the posts are formed on an inner surface of the receptacle, each of an outer surface of the receptacle and an inner surface of the closure member include threads, and the channels are disposed at an angle different from that of the threads.

In one embodiment of the sample collection method, the sealing member comprises a valve.

In one embodiment of the sample collection method, the closure member comprises an outer portion configured to seal with the second open end of the receptacle and an inner portion moveable relative to the outer portion, the sealing member comprises a disc fixed to the outer portion, and during the releasing step, the inner portion is displace relative to the outer portion thereby unseating the disc from the outlet.

In one embodiment of the sample collection method, a compressible member provided between at least a portion of the outer portion and the inner portion of the closure member, and during the releasing step, the compressible member is compressed between the inner portion and the outer portion.

In one embodiment, the sample collection device includes a sample receptacle having an inlet, a sample receiving member, and a closure member. The sample receptacle has a closed end and an open end. The sample receptacle may contain a stabilization fluid. The inlet may be closed by a valve member, such as a one-way valve, a flap or other mechanism to prevent leakage or spillage of the stabilization fluid while permitting the fluid coupling with the sample receiving member. The valve member is coupled to the inside of the sample receptacle near the open end. The sample receptacle may be sealed with a peelable member at the open end prior to collecting the sample. The peelable member ensures containment of the stabilization fluid and provides a visual indication of any tampering. The valve member may be self-resealable and may open only towards the stabilization fluid. The sample collection device may include a base for holding the sample receptacle.

As described herein, the sample collection device contains fewer parts and is easy to manufacture. The sample collection device has no complicated mechanism for retaining the stabilization solution. The sample collected is directly mixed with the stabilization solution. The sample collection device allows for simple, user-friendly collection of a sample, such as saliva, containing DNA. The sample collection device also reliably preserves the collected sample during transportation and storage thereof.

The method described herein relates to use of the sample collection device. The method may include the following steps: upon collecting the sample, the peelable member is peeled, the receiving member is inserted into the valve member and the sample is collected into the stabilization fluid through the receiving member; once the sample is collected, the receiving member is removed and the closure member is put onto the sample receptacle; the valve member closes upon removal of the receiving member. The method further provides a reliable mechanism of collecting a sample and preserving the sample throughout transportation, processing, and storage thereof.

In one embodiment, a sample collection device comprises a sample receptacle having an inlet, a sample receiving member and a closure member, wherein the sample receptacle has a closed end and an open end, the sample receiving member includes a larger first end for receiving the sample, and a smaller second end, and the inlet is coupled to the inside of the sample receptacle near the open end.

In one embodiment of the sample collection device, the sample receptacle is sealed with a peelable member at the open end prior to collecting the sample.

In one embodiment of the sample collection device, the inlet is closed by a valve or flap, openable upon insertion of one end of the sample receiving member to provide for a fluid communication.

In one embodiment of the sample collection device, the valve or flap is self-resealable.

In one embodiment of the sample collection device, the valve or flap is a one-way valve or flap.

In one embodiment of the sample collection device, the valve is a duckbill valve.

In one embodiment of the sample collection device, the smaller second end of the sample receiving member can be inserted into the inlet upon collection of the sample.

In one embodiment of the sample collection device, the sample receptacle further comprises a stabilizing fluid.

In one embodiment of the sample collection device, the sample receptacle is configured to hold 0.5 to 2.0 ml of sample.

In one embodiment of the sample collection device, the peelable member comprises aluminum lidding foil.

In one embodiment of the sample collection device, the peelable member comprises aluminum lidding foil and a heat based seal lacquer material.

In one embodiment, a sample collection system comprises the sample collection device and instructions for use.

In one embodiment, a method for collecting a sample using the sample collection device, comprises: peeling the peelable member, inserting the receiving member into the inlet and collecting the sample into sample receptacle through the receiving member, removing the receiving member once the sample is collected, and enclosing the sample receptacle using the closure member.

In one embodiment of the method, the sample comprising human saliva applied via expectorating from the mouth.

In one embodiment, a method for collecting a sample using the sample collection device, comprises: peeling the peelable member, inserting the receiving member into the inlet and collecting the sample into sample receptacle through the receiving member, removing the receiving member once the sample is collected, and enclosing the sample receptacle using the closure member.

In one embodiment of the method, the valve or flap closes upon removal of the receiving member.

In one embodiment of the method, the sample comprising human saliva is applied via expectorating from the mouth.

In one embodiment, the sample collection device includes a sample vessel, a sample receiving member and a closure member. The sample vessel has a closed end and an open end. The enclosed end may include an extended flat part. The sample receiving member is configured to be connectable to the open end of the sample vessel. The sample vessel may contain a stabilization composition. The sample vessel may be sealed with a peelable member at the open end prior to collecting the sample. The peelable member ensures containment of the stabilization composition and provides a visual indication of any tampering. The sample collection device may include a base for holding the sample vessel.

As described herein, the sample collection device contains fewer parts and is easy to manufacture. The sample collection device has no complicated mechanism for retaining the stabilization composition. The sample collected is directly mixed with the stabilization composition. The sample collection device allows for simple, user-friendly collection of a sample, such as saliva, containing DNA. The sample collection device also reliably preserves the collected sample during transportation and storage thereof.

The method described herein relates to use of the sample collection device. The method may include the steps of: supplying a user with the vessel sample collection device, for example, by postal services; collecting a sample such as saliva from the user; transporting the vessel sample collection device from the user's location to an analysis location; and thereafter processing and/or storing the sample. The method further provides a reliable mechanism of collecting a sample and preserving the sample throughout transportation, processing, and storage thereof.

In one embodiment, a sample collection device comprises a sample vessel, a sample receiving member, and a closure member, wherein the sample vessel has a closed end and an open end, the sample receiving member includes a larger first end for receiving the sample, and a smaller second end, and the sample vessel contains a stabilization composition.

In one embodiment of the sample collection device, the stabilization composition is a dry stabilization composition which dissolves upon contact with the sample.

In one embodiment of the sample collection device, the stabilization composition further comprises a liner which dissolves upon contact with the sample.

In one embodiment of the sample collection device, the stabilization composition is in the form of powder, tablet or capsule.

In one embodiment of the sample collection device, the sample receiving member is connected to the sample vessel.

In one embodiment of the sample collection device, the sample receiving member is not connected to the sample vessel.

In one embodiment of the sample collection device, the sample vessel has an extended flat part on the closed end.

In one embodiment of the sample collection device, the extended flat part has a barcode for easy identification and tracking.

In one embodiment of sample collection device, the sample vessel is sealed with a peelable member prior to collecting the sample.

In one embodiment, a sample collection system comprises the sample collection device and instructions for use.

In one embodiment, a method for collecting a sample using the sample collection device, comprising: activating the device, opening the closure member and collecting the sample through the sample receiving member connected to the sample vessel, closing the sample receiving member using the closure member, wherein the stabilization composition dissolves upon contact with the sample.

In one embodiment of the method, the sample comprises human saliva applied via expectorating from the mouth.

In one embodiment, the sample collection device includes a sampling member connected to a base, which may be by way of a stem, and a closure member configured to seal onto the base thereby sealing the sampling member within the closure member. The base includes a reservoir configured to contain a liquid to be mixed with the collected sample. The base is configured to release the fluid after the closure member has been sealed onto the base, thereby avoiding premature spillage of the fluid or contamination of the fluid.

As described herein, the sample collection device allows for simple, user-friendly collection of a sample, such as saliva or other sample containing DNA. The sample collection device may be provided in sizes suitable for a typical hand, and the sampling member may be configured to allow easy, efficient the collection of the sample from a user. The sample collection device may also reliably preserve and/or stabilize the collected sample during transportation and storage thereof. The sample collection device can provide clear indications of orientation of sampling member and stability of the base on a flat surface. Additionally, the closure member may be configured for easy connection with the base, and the sample collection device can provide consistent combining of a sample with a fluid, such as a stabilization fluid.

The method described herein relates to use of the sample collection device. The method may include the steps of: supplying a user with the sample collection device; collecting a sample from a user; transporting the sample collection device from the user's location to an analysis location; and thereafter processing and storing the sample. The user may be supplied with the sample collection device in any suitable manner, for example, by postal service or in-person in a clinical setting. The method further provides for reliably collecting a sample and preserving and/or stabilizing the sample throughout transportation, processing, and storage of the sample. This is because the method does not involve an unwieldy numbers of steps for use. And the method can provide fail safe methods for connecting a user record to a sample record. Also, the sample collection device is user-friendly and may include features to avoid contamination of the sample or tampering of the device, which provides reliable and consistent sampling.

In one embodiment, a sample collection device comprises a closure member having a first closed end and a second open end; a base including a reservoir contained within a body of the base; and a sampling member connected to the base configured to collect a sample, wherein the open end of the closure member is configured to seal onto the base over the sampling member, and wherein the reservoir includes a hollow body, and wherein the reservoir comprises an openable vent.

In one embodiment of the sample collection device, the reservoir further comprises a fluid contained within the hollow body of the reservoir.

In one embodiment of the sample collection device, the sample is a biological sample including nucleic acids and the fluid is a stabilization fluid capable of stabilizing nucleic acids.

In one embodiment of the sample collection device, the sampling member is connected to the base by a stem.

In one embodiment of the sample collection device, at least a portion of the stem is formed of a porous material.

In one embodiment of the sample collection device, the sampling member comprises a spherical pop.

In one embodiment of the sample collection device, the sampling member comprises a flavored or textured layer on an outer surface of the sampling member.

In one embodiment, a sample collection system comprises a sample collection device contained within a packaging, wherein the sample collection device comprises: a closure member having a first closed end and a second open end; a base including a reservoir contained within a body of the base; and a sampling member connected to the base configured to collect a sample, and wherein the open end of the closure member is configured to seal onto the base over the sampling member, and wherein the reservoir includes a hollow body, and wherein the reservoir comprises an openable vent.

In one embodiment, the sample collection system further comprises a collection bag configured to seal the sample collection device within the collection bag.

In one embodiment, the sample collection system further comprises a salivation inducing composition.

In one embodiment of the sample collection system, the salivation inducing composition is a layer provided on the sampling member.

In one embodiment, the sample collection system further comprises a return package, wherein the return package is configured to seal the sample collection device inside the return package.

In one embodiment of the sample collection system, the sample is a biological sample including nucleic acids and the fluid is a stabilization fluid capable of stabilizing nucleic acids.

In one embodiment, a sample collection method comprises the steps, in order, of: a depositing step of depositing a sample onto a sampling member, the sampling member being connected to a base; a sealing step of sealing an open end of a closure member onto the base, wherein the base includes a reservoir contained within a body of the base, the reservoir contains a fluid, and the reservoir includes an openable vent which is in a closed position; an opening step of opening the vent such that the vent is in an open position; and an inverting step of inventing the sealed closure member and base thereby releasing the fluid from the reservoir into the closure member.

In one embodiment of the sample collection method, the sampling member is connected to the base by a stem.

In one embodiment of the sample collection method, at least a portion of the stem is formed of a porous material.

In one embodiment of the sample collection method, the sampling member comprises a spherical pop.

In one embodiment, the sample collection method further comprises a shaking step after the inverting step wherein the sealed base and closure member are agitated to disperse the sample into the fluid.

In one embodiment of the sample collection method, the sample is a biological sample including nucleic acids and the fluid is a stabilization fluid capable of stabilizing nucleic acids.

In one embodiment of the sample collection method, the vent comprises a first layer and a second layer, each of the first layer and the second layer including a respective opening, and at least one of the first layer or the second layer is moveable relative to the other of the first layer or the second layer as to align the respective openings, thereby opening the sealing member during the opening step.

In one embodiment, the sample collection device includes a receptacle, a sampling member, and a closure member configured to seal the receptacle. Within the receptacle or closure member is provided a fluid, for example, a stabilization fluid. The closure member or receptacle may also include a peel foil on an end of the closure member or the open end of the receptacle.

As described herein, the sample collection device allows for simple, user-friendly collection of a sample, such as saliva or other sample containing DNA. The sample collection device may be provided in sizes suitable for a typical hand, and the receptacle may be configured to allow easy, efficient the collection of the sample from a user. The sample collection device may also reliably preserve and/or stabilize the collected sample during transportation and storage thereof. The sample collection device can provide clear indications of orientation of the receptacle and stability of the receptacle on a flat surface. Additionally, the closure member may be configured for easy connection with the receptacle, and the sample collection device can provide consistent combining of a sample with a fluid, such as a stabilization fluid.

The method described herein relates to use of the sample collection device. The method may include the steps of: supplying a user with the sample collection device; collecting a sample from a user; transporting the sample collection device from the user's location to an analysis location; and thereafter processing and storing the sample. The user may be supplied with the sample collection device in any suitable manner, for example, by postal service or in-person in a clinical setting. The method further provides for reliably collecting a sample and preserving and/or stabilizing the sample throughout transportation, processing, and storage of the sample. This is because the method does not involve an unwieldy numbers of steps for use. And the method can provide fail safe methods for connecting a user record to a sample record. Also, the sample collection device is user-friendly and may include features to avoid contamination of the sample or tampering of the device, which provides reliable and consistent sampling.

In one embodiment a sample collection device comprises: a receptacle having a first closed end and a second open end; a closure member configured to seal the second open end of the receptacle; and a sampling member configured to collect a sample, and wherein the receptacle contains a fluid, and wherein the receptacle and closure member are configured to seal the sampling member within the receptacle.

In one embodiment of the sample collection device, the sample is a biological sample including nucleic acids and the fluid is a stabilization fluid capable of stabilizing nucleic acids.

In one embodiment of the sample collection device, the sampling member is chewing gum.

In one embodiment of the sample collection device, the sampling member is a spherical pop.

In one embodiment of the sample collection device, at least a portion of the sampling member is formed of a porous material.

In one embodiment of the sample collection device, the receptacle comprises a peel foil covering the open end of the receptacle.

In one embodiment of the sample collection device, the sampling member comprises a flavored or textured layer on an outer surface of the sampling member.

In one embodiment, a sample collection system comprises a sample collection device contained within a packaging, wherein the sample collection device comprises: a receptacle having a first closed end and a second open end; a closure member configured to seal the second open end of the receptacle; and a sampling member configured to collect a sample, and wherein the receptacle contains a fluid, and wherein the receptacle and closure member are configured to seal the sampling member within the receptacle.

In one embodiment, the sample collection system further comprises a collection bag configured to seal the sample collection device within the collection bag.

In one embodiment, the sample collection system further comprises a salivation inducing composition.

In one embodiment of the sample collection system, the salivation inducing composition is a layer provided on the sampling member.

In one embodiment, the sample collection system further comprises a return package, wherein the return package is configured to seal the sample collection device inside the return package.

In one embodiment of the sample collection system, the sample is a biological sample including nucleic acids and the fluid is a stabilization fluid capable of stabilizing nucleic acids.

In one embodiment, a sample collection method comprises the steps, in order, of: a depositing step of depositing a sample onto a sampling member; a transferring step of transferring the sampling member into an open end of a receptacle, wherein the receptacle contains a fluid; and a sealing step of sealing a closure member onto the open end of the receptacle.

In one embodiment of the sample collection method, the sampling member is chewing gum.

In one embodiment of the sample collection method, at least a portion of the sampling member is formed of a porous material.

In one embodiment of the sample collection method, the sampling member comprises a spherical pop.

In one embodiment, the sample collection method further comprises a shaking step after the sealing step wherein the sealed receptacle and closure member are agitated to disperse the sample into the fluid.

In one embodiment of the sample collection method, the sample is a biological sample including nucleic acids and the fluid is a stabilization fluid capable of stabilizing nucleic acids.

The sample collection device and method are especially useful for collection of a human saliva sample, transportation of the sample to an analysis location, and storage of the sample. In some embodiments, the sample collection device and method are useful for in-home collection by the user.

BRIEF DESCRIPTION OF DRAWINGS

FIGS. 5A-5B are partial sectional views demonstrating a sealing step for the sample collection device, in accordance with an embodiment.

FIG. 11 is a schematic demonstrating a collection method using the vessel sample collection device.

FIG. 16 is a perspective view demonstrating a collection method using the sample collection device.

The figures depict embodiments of the present disclosure for purposes of illustration only. One skilled in the art will readily recognize from the following description that alternative embodiments of the structures and methods illustrated herein may be employed without departing from the principles, or benefits touted, of the disclosure described herein.

DETAILED DESCRIPTION

I. System Environment

The present description relates to multiple examples of sample collection devices and methods for providing a user with the sample collection device, collecting a sample from the user, mixing the sample with a fluid, transporting and storing the mixed sample, and analyzing the sample thus collected. Non-limiting embodiments of the sample collection device and method of using the sample collection device are described below with reference to the drawings.

I. Sample Collection I

I.A. Sample Collection Device

The sample collection device includes a receptacle for collecting the sample. The receptacle is not particularly limited in shape or form. Some embodiments of the receptacle include containers such as a can, box, tube, or other suitable vessels. The material forming the receptacle is not particularly limited and may include, for example, plastic or metal. Additionally, the receptacle may include a coating on its inner surface, such as a frictionless coating to prevent the sample from adhering to the inner surface of the receptacle, thereby minimizing evaporation of the sample and ensuring thorough mixing of the sample with the fluid once combined. Other coatings may contain a dissolvable material to be further mixed with the sample.

Figure 1:
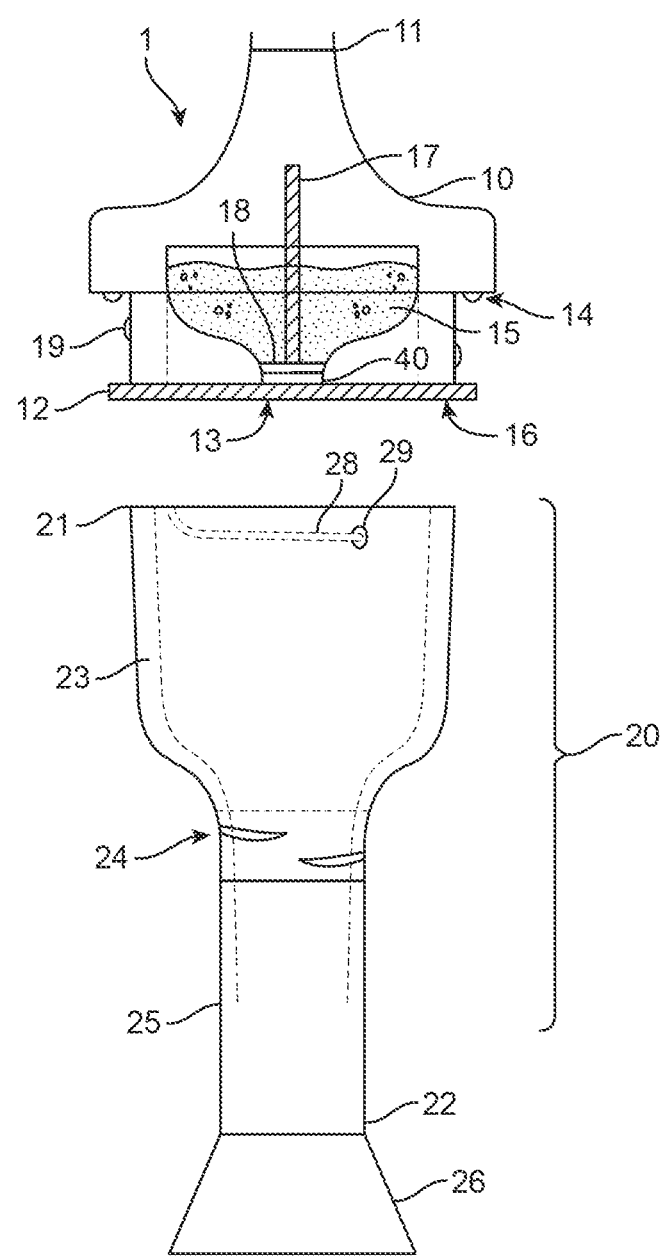
FIG. 1 is a side of a sample collection device, in accordance with an embodiment.

Referring to FIG. 1, the sample collection device 1 may include a sample tube 20 and a cap 10. The sample tube 20 includes an open first end 21 and a closed second end 22.

The first end 21 has a collection portion, into which a sample is deposited. The collection portion is not particularly limited, but may be configured to allow a user to easily deposit the sample into the receptacle. When the sample to be collected is saliva, the collection portion may include an opening large enough to permit a user to spit or otherwise deposit the saliva into the receptacle. In some embodiments, the collection portion may be funnel-shaped. Such a configuration provides a collection portion that is large enough to allow easy sampling while the remainder of the receptacle maintains a reduced size as compared to the funnel portion in order to provide a conveniently-sized, for example, handheld, sample collection device. This configuration may also reduce the internal surface area of the receptacle, such that the sample more efficiently pools within the receptacle, which facilitates more thorough mixture with the fluid and avoids loss of sample due to evaporation.

In an exemplary embodiment shown in FIG. 1, the first end 21 includes a funnel portion 23 for collecting the sample. In such embodiments, the sample tube 20 may be integrally formed with funnel portion 23, or the sample tube 20 may further comprise a connection 24 between the funnel portion 23 and the body portion 25 of the sample tube 20, as shown in FIG. 1. In embodiments wherein the sample tube 20 and the funnel portion 23 are separately formed, the connection 24 may be configured such that the funnel portion 23 cannot be removed from the body portion 25 by the user. This prevents tampering with the sample to ensure reliable analysis results. Additionally, in some embodiments, the connection 24 may be configured to be disengaged by a technician, for example, using a specially-adapted tool, at the analysis location for easier access to the sample.

Figure 7A:
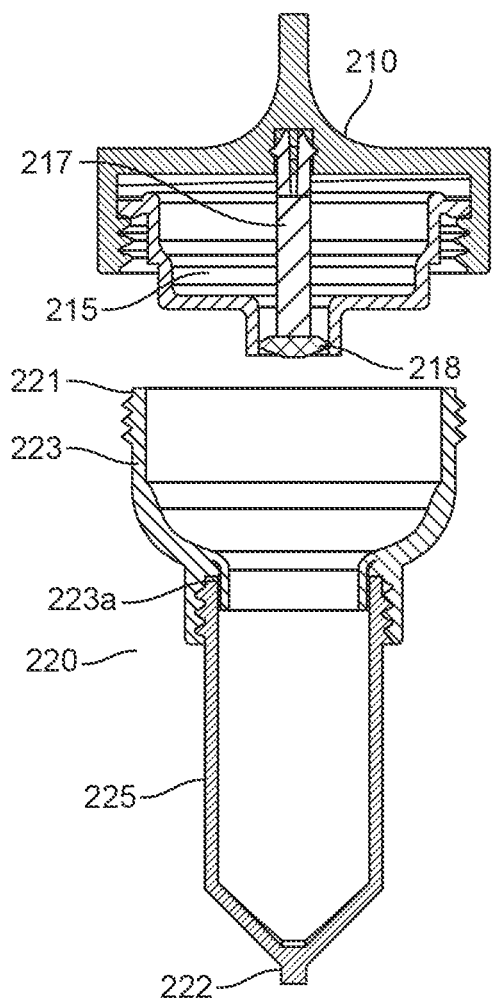
FIG. 7A is a cross sectional view of the sample collection device, in accordance with an embodiment.

The connection 24 between the funnel portion 23 and the body portion 25 can include, for example, a threaded portion, a welded portion, or an adhesive portion. The threaded portion may include, for example, a thread with locking features. In some embodiments, the funnel portion 23 and the body portion 25 are nested at the connection 24. In such a configuration, one of the funnel portion 23 and the body portion 25 is provided with an inner diameter equal to or greater than the outer diameter of the other, and thereby the funnel portion 23 and the body portion 25 overlap one another to ensure a secure seal and to avoid leakage of the sample. An example of this configuration is shown in FIG. 7A, wherein funnel portion 223 is threaded onto the body portion 225 of the sample tube 220. Further, as shown in FIG. 7A, since the funnel portion 223 is sealed to an outer surface of the body portion 225, the funnel portion 223 includes an overlapping portion 223a which fits inside of the body portion 225 to further ensure a tight seal and to avoid leakage.

Figure 6A:
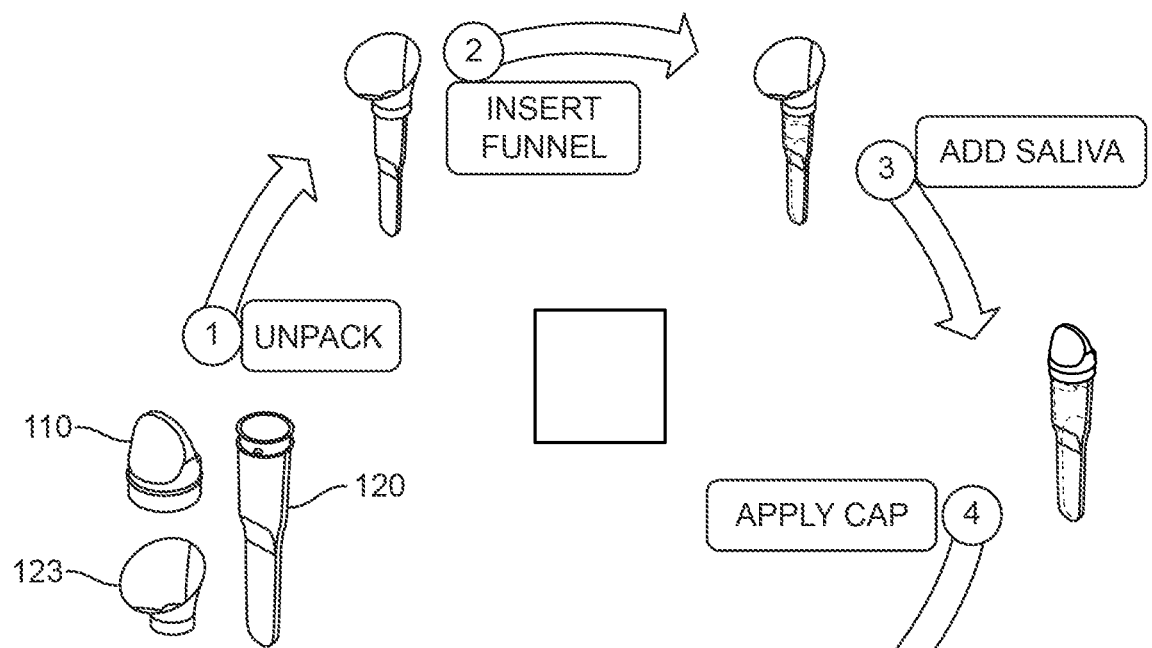
FIGS. 6A-6B are schematics showing a method of sample collection with the sample collection device, in accordance with an embodiment.
Figure 6B:
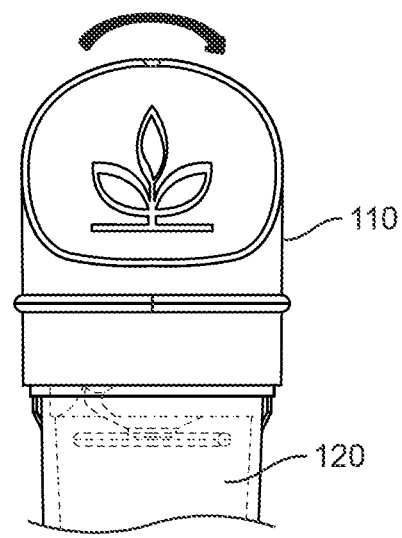

In another embodiment, the sample collection device may include a separate collection portion, such as the funnel 123 shown in FIG. 6A. In such an embodiment, the funnel 123 may be inserted into or onto the sample tube 120 in order to allow for easy collection of a sample. Thereafter, the funnel 123 may be removed to allow the closure member, such as cap 110, to seal onto sample tube 120.

The shape of the body portion 25 is not particularly limited and may be substantially cylindrical, conical, or prismatic. Additionally, the diameter or width of the body portion 25 is not particularly limited and may be uniform or variable along the length of sample tube 20. In some embodiments, the body portion 25 may be 10 mm, 15 mm, or 20 mm wide. For example, the minimum width of the body portion 25 may be not less than 1 mm, not less than 3 mm, not less than 5 mm, or not less than 10 mm, in order to allow for thorough mixing between the sample and the liquid. The maximum width of the body portion 25 may be, for example, not more than 40 mm, not more than 30 mm, not more than 20 mm, or not more than 15 mm, in order to ensure sufficient pooling of the sample.

Figure 4:
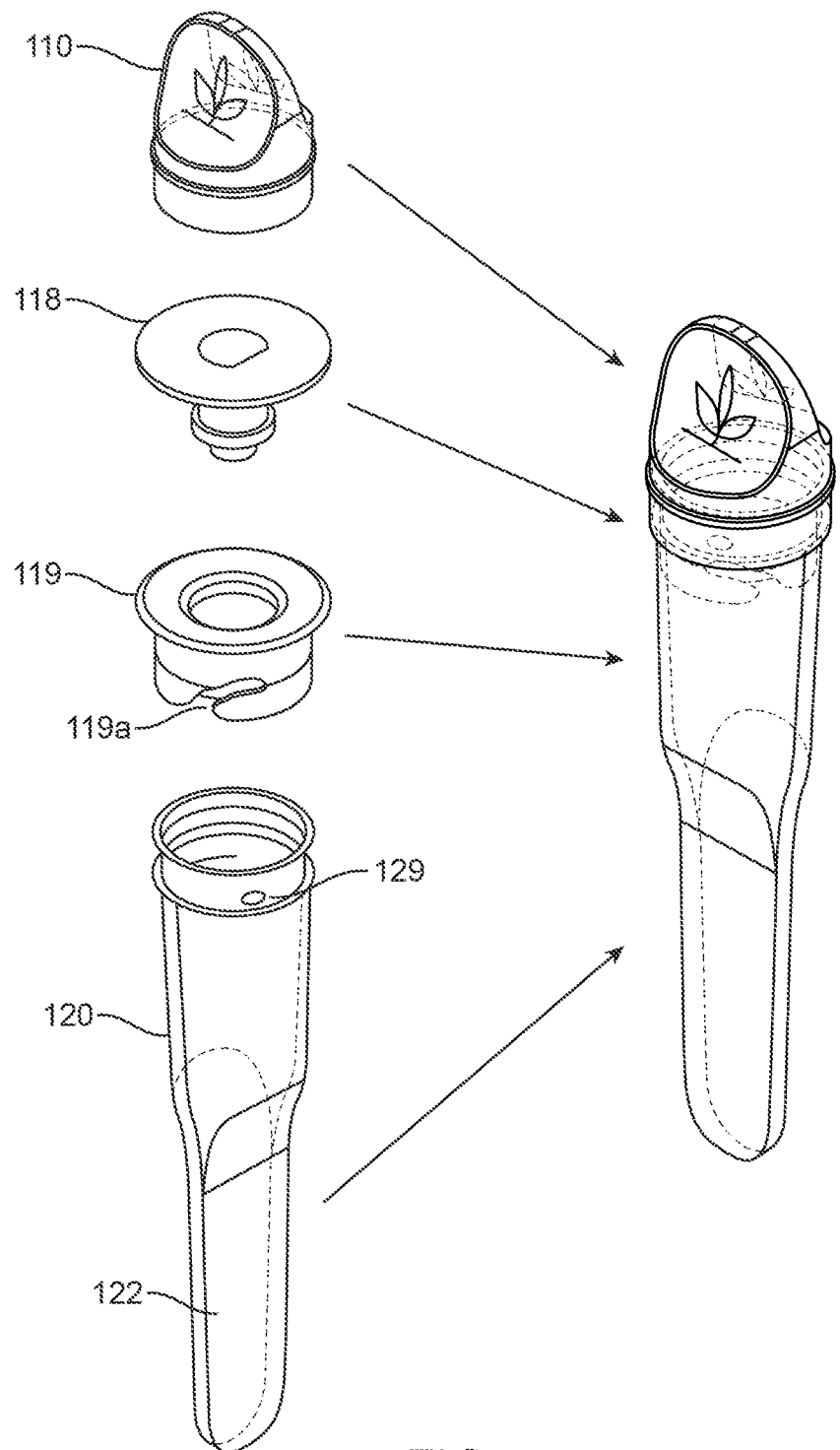
FIG. 4 is an exploded view of the sample collection device, in accordance with an embodiment.

In another embodiment, the receptacle may have a flattened portion, such as flattened portion 122 shown in FIG. 4. The flattened portion 122 provides the user with an easy grip for sample and provides additional leverage on the sample tube 120 when sealing the cap 110 onto the sample tube 120. A similar configuration is also shown in FIG. 7A, wherein sample tube 220 includes a flattened portion 222.

In one embodiment, the sample collection device 1 includes a base in order to stably support the sample collection device 1 in an upright position to allow for ease of collection and to avoid spillage of the sample. The base is not particularly limited and may be, for example, an integral portion of the sample tube 20 or a separate base member 26, an example of which is shown in FIG. 1. Where the base is an integral portion of the sample tube 20, the second end 22 may include a substantially flat portion thereby forming the base or the sample tube 20 may be flared at the second end 22 to provide an enlarged base. When a separate base member 26 is used, the base member 26 is configured to maintain sample tube 20 in an upright position. The base member 26 may be formed of any suitable material, such as rubber or plastic. In some embodiments, the base member 26 is permanently attached to the sample tube 20 in a suitable manner, such as an adhesive or a weld. In other embodiments, the base member 26 may be detachable. For example, the base member 26 may reversibly screw onto the sample tube 20 or the base member 26 may include an interior depression into which the sample tube 20 is placed. In some embodiments, the base member 26 has a flared shaped with an enlarged, flat bottom, as shown in FIG. 1. In other embodiments, a stand may be integrated into a packaging for the sample collection device 1. For example, the packaging may include a cutout portion into which the sample tube 20 fits.

Further, the body portion 25 may have an outer surface thereof marked with one or more lines or other indicators representing, for example, a threshold volume of sample to be collected or a volume of the contents of the sample tube 20. In the case of a saliva sample, the threshold volume line may be set at, for example, one or more of 0.5 ml, 0.75 ml, 1 ml, 1.5 ml, 2 ml, 3 ml, 4 ml, 5 ml, 6 ml, 7 ml or 10 ml.

As shown in FIG. 1, the funnel portion 23 is tapered, with a diameter or width thereof increasing toward the first end 21. The degree of tapering of the funnel portion 23 is not particularly limited, but may be configured to allow for sufficient movement of a sample from the first end 21 to the second end 22 of the sample tube 20. For example, assuming the sample is a viscous liquid such as saliva, a wall of the funnel portion 23 may be disposed at an angle of no more than 60° relative to the sample tube 20, or no more than 45°, or no more than 35°.

The funnel portion 23 may be configured to allow a user to easily deposit a sample into the sample tube 20. As such, in one embodiment, the funnel portion 23 has a diameter at the first end 21 large enough to accommodate depositing the sample from the user, such as saliva from a user's mouth. However, when the funnel portion 23 is too large, the interior surface of the funnel portion 23 is increased which may lead to insufficient collection of the sample due to sample remaining on the surface of the funnel portion 23, and loss of sample due to increased evaporation of the sample over the surface area of the funnel portion 23. Accordingly, in some embodiments, the diameter of the funnel portion 23 at the first end 21 may be in the range from 10 to 50 mm, or 15 to 40 mm, or 20 to 30 mm.

Additionally, the shape of the funnel portion 23 is not particularly limited and may be substantially cylindrical, or conical or prismatic. The funnel portion 23 may also include a lip at the first end 21 configured to, for example, facilitate collection of the sample, avoid spillage of the sample during collection, and provide added comfort to the user.

The sample collection device 1 includes a closure member configured to seal the receptacle. The closure member may be formed of any suitable material, such as rubber, plastic, or metal. The size and shape of the closure member are not particularly limited so long as the closure member may attach to and reliably seal the receptacle. The closure member may seal the receptacle in any suitable manner, such as by threads included on each of the closure member and the receptacle, an adhesive between the closure member and the receptacle, a latch, or other sealing mechanisms known in the art. Further, the closure member may irreversibly lock onto the receptacle in order to prevent contamination or tampering. In such embodiments, if the sample collection is tampered with, the seal between the closure member and the receptacle may show evidence of such tampering, such a breakage or another indicator. Additionally, a gasket may be included at the seal on either or both of the receptacle and the closure member to ensure a tight seal and to prevent leakage.

Figure 3A:
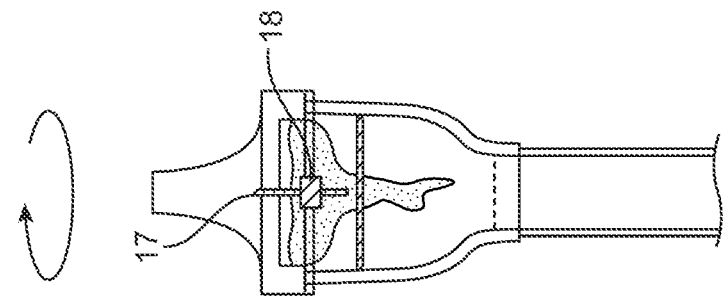
FIGS. 3A-3D are schematics demonstrating a method of sample collection, in accordance with an embodiment.
Figure 3B:
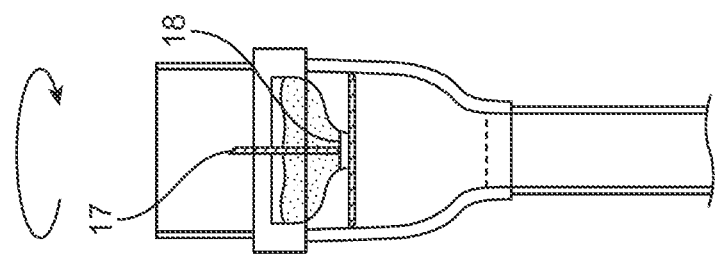
Figure 3C:
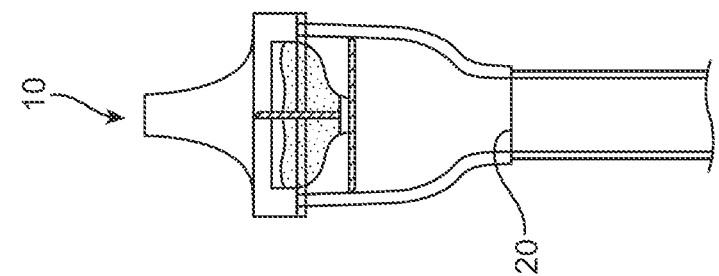

In an embodiment shown in FIG. 1, the closure member is a cap 10. The cap 10 includes a first cap end 11 and a second cap end 12. The cap 10 is configured to connect to the first end 21 of the sample tube 20. In the embodiment shown in FIG. 1, the cap 10 includes one or more nodules 19 configured to communicate with slot 28 provided on an interior surface of the sample tube 20 at the first end 21. In such an embodiment, the cap 10 may be sealed onto sample tube 20 by aligning the nodule 19 with slot 28, and inserting nodule 19 into the slot 28. Thereafter, the cap 10 is rotated relative to the sample tube 20 until nodule 19 reaches locking groove 29. Slot 28 and locking groove 29 may be configured to lock nodule 19 in place once nodule 19 has reached locking groove 29, for example, by allowing nodule 19 to deform into locking groove 29. In other embodiments, the cap 10 may include threads on the inside of the cap 10 near the second cap end 12, wherein the sample tube 20 includes complimentary threads on an outer portion near the first end 20. In some embodiments, the sealing mechanism provides a tactile indication notify the user that the closure member has been sealed onto the receptacle. The tactile indication may be a sound or a visual marker, such as alignment lines provided on the closure member and the receptacle. For example, as shown in FIG. 3C, once the nodule 19 has locked into the locking groove 29, an audible click sound is produced to notify the user that the cap 10 has been sealed onto sample tube 20.

In other embodiments, the closure member such as cap 110 may include a lock ring 119, as shown in FIG. 4. In such embodiments, the lock ring 119 may be mechanically assembled as shown in FIG. 5A. Also, the lock ring 119 is configured to be moveable within cap 110 such that it can be spaced from a fluid retention disc 118 thereby allowing fluid to be released from a reservoir 115 within the cap 110. Specifically, the lock ring 119 may be actuated by one or more posts 129 provided on an inner surface of the sample tube 120. In this embodiment, threads are provided on both an inner surface of the cap 110 and an outer surface of the sample tube 120. Additionally, the lock ring 119 is configured to fit inside of the opening of the sample tube 120 and is provided with one or more channels 119a configured to allow posts 129 to run along the channels 119a. The channels 119a are angled such that, when the cap 110 is twisted onto the threads of the sample tube 120, the posts 129 move along channels 119a to apply a mechanical advantage above what the threads on the outer surface of the sample tube 120 supply. This causes the lock ring 119 to displace toward the sample tube 120, away from fluid retention disc 118. By this configuration, the fluid is released from reservoir 115 as the cap 110 is sealed, i.e., threaded, onto the sample tube 120.

In some embodiments, the fluid retention disc 118 is configured to release the fluid within the reservoir 115 after the cap 110 has been sealed onto the sample tube 120. The fluid retention disc 118 may be a separate member, mechanically assembled in the cap 110 as shown in FIG. 5A, or may be an integrally formed portion of the cap 110. In one embodiment, the fluid retention disc 118 includes one or more fluid channels 118a acting as outlets and configured to allow the fluid to flow therethrough from the reservoir 115 into the sample tube 120. The number of fluid channels 118a and size thereof may vary depending on the intended application, for example, depending on the viscosity of the fluid in the reservoir 115.

In other embodiments, the lock ring 119 may be unseated by a user pulling the cap 110 away from the sample tube 120 after the cap 110 has been sealed onto the sample tube 120. In such embodiments, the fluid retention disc 118 is locked to the cap 110 and configured to unseat from the lock ring 119 when the cap 110 is pulled.

Figure 5B:
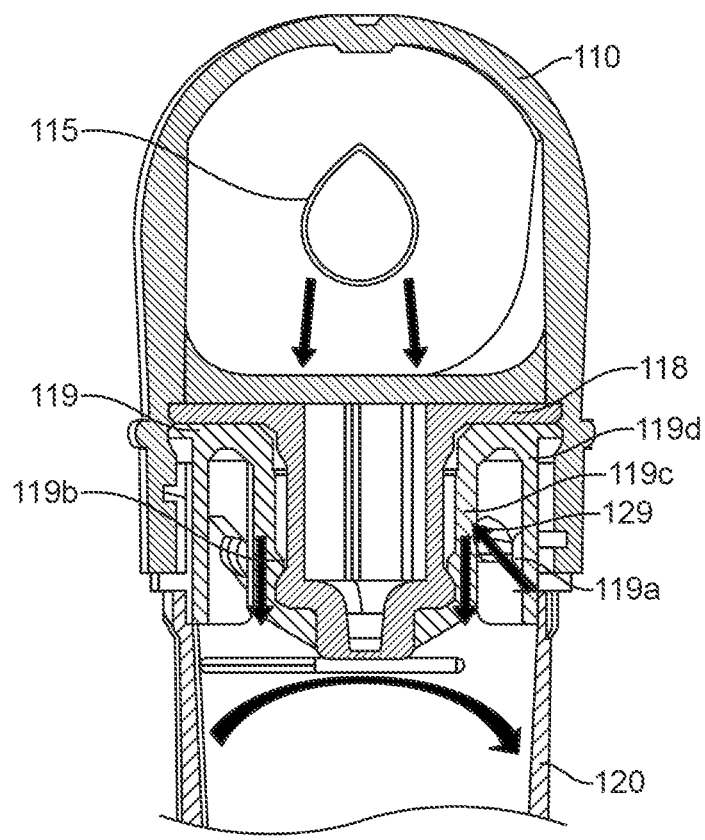

In one embodiment shown in FIG. 5B, the lock ring 119 has an inner cylindrical portion 119c and an outer cylindrical portion 119d, wherein the inner cylindrical portion 119c forms a valve seat engaged with fluid retention disc 118. When seated, the inner cylindrical portion 119c seals the fluid channels 118a of the fluid retention disc 118. When unseated, the inner cylindrical portion 119c is displaced (downward) relative to the fluid channels 118a to allow the fluid to be released from reservoir 115.

In some embodiments, a distal end of the inner cylindrical portion 119c does not protrude past a distal end of outer cylindrical portion 119d. Such a configuration may prevent a user from inadvertently pulling on the lock ring 119 and preemptively releasing the fluid.

In some embodiments, when the cap 110 is not attached to sample tube 120, the lock ring 119 is locked in contact with fluid retention disc 118 to avoid any leakage of the fluid. In some embodiments, this is may be achieved by including a cuff-link portion 119b on the lock ring 119 as shown in FIG. 5B. Prior to the cap 110 being threaded onto the sample tube 120, the lock ring 119 is locked onto the fluid retention disc 118 via the cuff-link portion 119b. That is, in these embodiments, the lock ring 119 may be snap-fit onto the fluid retention disc 118. After the cap 110 is threaded onto the sample tube 120, the downward forced caused by the angle of channel 119a pulls the lock ring 119 free from the fluid retention disc 118. The materials used for the lock ring 119 and the fluid retention disc 118 are no particularly limited and may, for example, include plastic. The materials forming the lock ring 119 and the fluid retention disc 118 may be flexible materials to allow the lock ring 119 to become unseated from the fluid retention disc 118.

Further, cap 110 may include a tamper-proof seal covering any exposed portions of the lock ring 119 and/or the fluid retention disc 118. For example, the cap 110 may include a shrink wrap seal or a peel foil. The tamper-proof seal may be configured to be easily removed by the user such as a pull tab or perforated portion. Also, in some embodiments, the tamper-proof seal shows tampering by physical damage or otherwise. The tamper-proof seal may serve to prevent a user from inadvertently unseating the lock ring 119 from the fluid retention disc 118 by, for example, pulling on the lock ring 119.

Figure 7B:
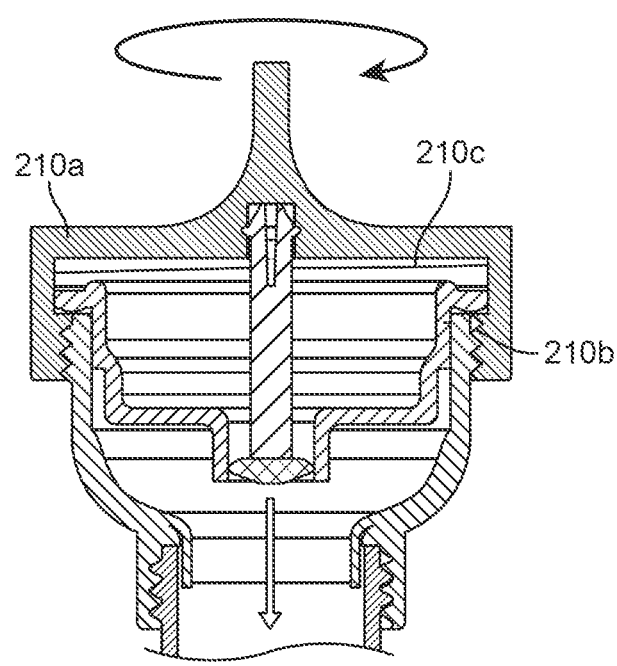
FIGS. 7B-7C are schematics demonstrating a sealing step for the sample collection device, in accordance with an embodiment.
Figure 7C:
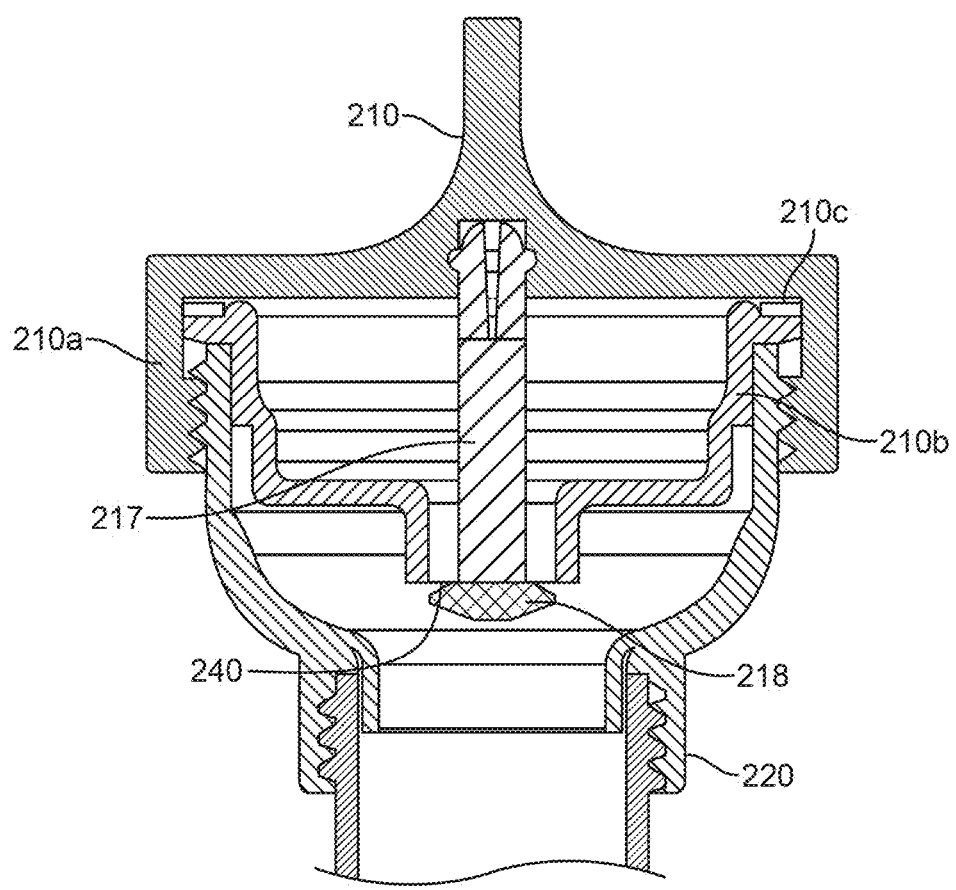

In the embodiment shown in FIGS. 7A-7C, the cap 210 is formed of an outer cap body 210a and inner cap body 210b. The inner cap body 210b includes a hollow reservoir 215 and is moveable relative to the outer cap body 210a. The hollow reservoir 215 is sealed by a disc 218 which is fixed to the outer cap body 210a by way of a stem 217. When the cap 210 is not sealed onto the sample tube 220, the outlet 240 of reservoir 215 is sealed by disc 218 seated on the outlet 240. When the cap 210 is not sealed onto the sample tube 220, the outer cap body 210a and the inner cap body 210b are spaced from one another by a compressible member 210c. The compressible member 210c may be, for example, a wave spring, as shown in FIGS. 7A-7C. The compressible member 210c may be a separate component, or may be integrally formed with either of the outer cap body 210a or the inner cap body 210b. The compressible member 210c is configured to compress when the cap 210 is sealed onto the sample tube 220, thereby allowing the inner cap body 210b to displace toward outer cap body 210b, as shown in FIG. 7C.

In this embodiment, the cap 210 is sealed onto the sample tube 220 by, for example, threads provided on an outer surface of the sample tube 210 near the first end 221 and complimentary thread provided on an inner surface of the outer cap body 210a. As the cap 210 is threaded onto the sample tube 220, the inner cap body 210b is displaced toward the outer cap body 210a thereby actuating the stem 217 and disc 218 and unseating the disc 218 from the outlet 240 of the reservoir 215. That is, since disc 218 is in a fixed relationship relative to outer cap body 210a, as inner cap body 210b displaces toward outer cap body 210a, the disc 218 unseats from the outlet 240 allowing the contents of reservoir 215 to be released into the body 225 of sample tube 220.

In one embodiment shown in FIG. 1, an inner diameter of the cap 10 at the second cap end 12 is greater than an outer diameter of the first cap end 11 of the sample tube 20, such that the cap 10 can overlap the sample tube 20. The inside of the cap 10 near the second cap end 12 may include a gasket 14 to aid in sealing the cap 10 to the sample tube 20. The gasket 14 may be formed of an elastomeric material such as rubber. In other embodiments, the gasket 14 is not included.

In some embodiments, the first cap end 11 is configured to be easily gripped by a user, for example, by a forefinger and thumb of the user. For example, the first cap end 11 may have a flattened shape such as a large twist tab, or the surface of the cap 10 may be textured with ridges or provided with a grip portion.

The closure member includes a reservoir within a body of the closure member. In some embodiments, the reservoir is separately formed from the closure member. This provides for easier manufacturing while allowing for easy inspection of the reservoir for leaks or other irregularities. In other embodiments, the reservoir may be integrally formed with the closure member.

The reservoir includes a hollow body capable of containing a liquid to be mixed with a collected sample. The interior volume of the reservoir may be, for example, 0.1 ml to 20 ml. The reservoir may be formed of any suitable material, but the material for the reservoir should not be reactive with the fluid to be contained within the reservoir as to avoid contamination or leakage. The shape and size of the reservoir is not particularly limited, but the reservoir is configured to fit within the closure member.

Referring to FIG. 1, the reservoir may be a capsule 15. The capsule 15 is contained within the body of the cap 10. The capsule 15 can include a fluid such as a stabilization fluid for stabilizing the sample after collection, during transportation and storage. For example, a stabilization fluid may be included to stabilize sample nucleic acids contained within a saliva sample. In some embodiments, the capsule can hold 0.25 ml to 2 ml of stabilization fluid, or 0.1 to 5 ml, or 0.5 to 3 ml, or 0.5 to 1.5 ml, or 0.5 to 1.0 ml, or about 0.75 ml of stabilization fluid. In some embodiments, the stabilization fluid includes an alcohol, at least one detergent, and at least one salt. Further, a buffer may be included in the stabilization fluid in order to maintain a constant pH. In one embodiment, the stabilization fluid includes the following Formula 1 of DNA preserving solution described in I.B. Stabilization Fluid.

Additionally, the reservoir includes an outlet through which the contents of the reservoir may be released into the receptacle. The outlet is sealed by a sealing member. The sealing member is configured to remain in a closed position until after the closure member has been sealed onto the receptacle. This prevents possible leakage of the contents of the reservoir. In some embodiments, when the sealing member is moved to an open position, a tactile indication is provided to notify the user. Such an indication may be an audible noise, or the fluid within the reservoir may be colored to provide visual confirmation that the outlet is open. For example, in FIG. 3D, opening the outlet provides an auditory click as well as visual confirmation from the colored liquid, thereby ensuring that the fluid within the reservoir is released into the receptacle. Such features safeguard against the sample being left isolated from the fluid, wherein the sample could degrade prior to analysis.

Figure 3D:
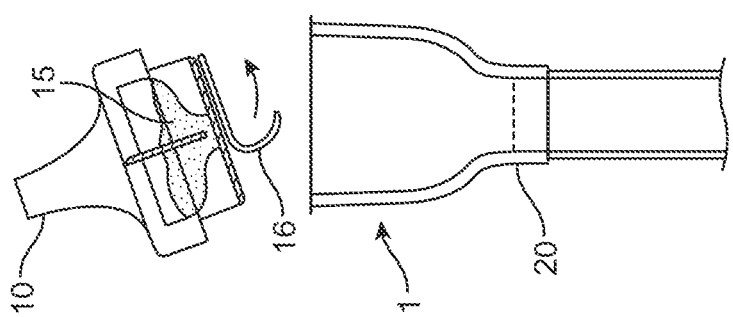

The sealing member may be, for example, a valve, particularly a one-way valve or a check valve. For example, referring to FIG. 1, the capsule 15 includes a valve 13 near the second cap end 12, which seals outlet 40. The valve 13 may be configured to be opened, i.e., to allow communication between the interior of the capsule 15 and the interior of sample tube 20, by rotation of the cap 10 relative to the sample tube 20. In one embodiment as shown in FIG. 1, the valve 13 includes an elongated threaded member 17 and a disc 18 seated on the outlet 40. After the cap 10 has been sealed onto the sample tube 20, the disc 18 is configured to move along threaded member 17 and unseat from outlet 40 when the cap 10 is rotated. As shown in FIG. 3D, the rotation of the cap 10 unseats disc 18 from the outlet 40 whereby disc 18 moves along the threaded portion 17.

In another embodiment, the sealing member, such as a check valve, may be opened from pressure created in the process of sealing the closure member onto the receptacle. In another embodiment, the sealing member may include two layers each including one or more openings, at least one of the layers being moveable relative to the other layer. In this embodiment, when the openings of the respective layers are not aligned, the outlet is sealed, and when the openings of the respective layers are aligned, the outlet is unsealed and flow of fluid from the reservoir is permitted through the openings of the layers. In this embodiment, the layers may be aligned by, for example, twisting the closure member after it has been sealed onto the receptacle.

In one embodiment, the closure member may include a peel foil covering the end of the closure member near the outlet. Since the surface of the closure member sealing onto the receptacle may come into contact with the sample, the peel foil prevents any possible contamination of the sample from the closure member. For example, in FIG. 2, the cap 10 includes a peel foil 16 located at the second cap end 12, enclosing the capsule 15. The peel foil 16 may be manufactured from, for example, a metallic foil such as an aluminum lidding foil. The foil can be 15-50 micrometers thick, for example, 20 micrometers or 25 micrometers thick. The foil can include a heat seal lacquer material for pharmaceutical applications requiring a welded seal to polypropylene. Examples of materials for the seal include TEKNILID 1254 product and TEKNILID 1256 product (TEKNIPLEX, Tekini-Films USA, Somerville, NJ). Properties of the seal include resistance to breakage during manufacture and transport to the user and before peeling. Also, the seal may be provided with the ability to withstand corrosion caused by the fluid in case the sealing member prematurely opens. Further, the peel foil 16 may include a pull tab or weakened portion to provide easy removal by the user.

I.B. Stabilization Fluid

In some embodiments, the stabilization fluid includes an alcohol, at least one detergent, and at least one salt. Further, a buffer may be included in the stabilization fluid in order to maintain a constant pH. In one embodiment, the stabilization comprises Formula 1 including the following with the respective concentration for each:

| Formula 1 | Concentration |
| --- | --- |
| Alcohol SDA 3C (95% EtOH/5% IPA) | 40% v/v/ |
| N-Acetylcysteine (FW = 163.2) | 6 mM |
| Sodium Lauryl Sulfate (SDS) | 0.1% w/w |
| Tris HCL, PH 7.5 | 0.3M |
| EDTA Disodium Dihydrate, pH 8.0 | 20 mM |
| NaOAc•3H$_2$O (sodium acetate trihydrate) | 0.5M |
| Ticlosan | 0.1% w/w |

The pH of the stabilization fluid of Formula 1 above, both before sample collection and after sample collection may be about 8, or from 7.9-8.2, 7.0-7.5, 7.4-7.8, or 7.5-8.0. The pH of the stabilization fluid of Formula 1 is consistent since it is a buffered solution. In general, saliva is naturally weakly buffered with a pH range of 5.9-7.9. It is affected by food, drink and age (adults on the more acidic side; children on the basic side).

Acceptable stabilization fluids for use in the methods and devices described herein may include those disclosed, for example, in U.S. Pat. No. 7,297,485 B2, U.S. Pat. No. 9,523,115 B2, U.S. Pat. No. 6,548,256 B2, U.S. Pat. No. 7,303,876 B2, U.S. Pat. Nos. 8,425,864, 6,428,962, WO Patent Publication No. 93/03167, WO Patent Publication No. 98/44158, WO Patent Publication No. 99/39010, U.S. Pat. Nos. 4,935,342, 6,048,091, 8,470,536, 8,158,357, 7,482,116, 9,416,356, 9,410,147, 7,214,484, 6,939,672, 8,431,384, 7,589,184, 9,040,675, and 6,992,182 B1, all of the contents of which are hereby incorporated by reference in their entirety.

In another embodiment, the stabilization fluid includes one or more of a chelating agent, a denaturing agent, and a reducing agent. Also, the stabilization fluid may contain a compound that reduces the viscous properties of mucin, thereby facilitating the extraction of nucleic acids contained in the sample. The stabilization fluid may be configured to stabilize nucleic acids, inhibit nucleases that may be present in a saliva sample, and be compatible with proteolytic enzymes and other reagents used to purify/amplify oligo- or polynucleotides.

In another embodiment, the stabilization composition may contain a compound that reduces the viscous properties of mucin, thereby facilitating the extraction of nucleic acids contained in the sample. The stabilization composition may have the ability to stabilize nucleic acids, inhibit nucleases that may be present in a saliva sample, and be compatible with proteolytic enzymes and other reagents used to purify/amplify oligo- or polynucleotides.

I.C. Sample Collection System

Also provided is a sample collection system. The sample collection system includes a packaging containing the sample collection device. In some embodiments, each sample collection system includes a unique identifier, such as a number. The unique identifier matches the collected sample to the user, ensuring that analysis results are properly associated with the user. The unique identifier may be provided, for example, on one or both of the closure member and the receptacle, as well as on the packaging.

The sample collection system may be administered at a clinical location or in-home by the user and the contents of the packaging may vary depending on the intended use. In some embodiments, the packaging includes instructions for use of the sample collection device and sample collection system. The instructions may direct the user to activate an online account and enter personal information and/or the unique identifier to ensure accurate processing. In some embodiments, the instructions guide the user or clinical technician through the collection method, including at least depositing the sample into the receptacle, sealing the closure member over the receptacle, and opening the sealing member to mix the sample with the fluid contained within the reservoir.

Further, within the packaging, the sample collection device may be provided in a sealed wrapper in order to prevent contamination. The sealed wrapper may be made of any appropriate material. The closure member and receptacle may be included in a single sealed wrapper or in two separate sealed wrappers. The sealed wrappers may include a portion, such as a perforated portion or a pull tab, to allow for easy opening by the user. The packaging may also include a collection bag in which the user places the sample collection device after collection is complete. The collection bag may be sealable to prevent contamination during transport of the sample. The packaging may include additional items, for example, in the case of collecting saliva, the packaging may include a salivation inducing member, such as piece of gum.

The packaging may include a sealable package for transporting the collected sample from the user's location to the analysis location. Alternatively, the packaging may be resealable and configured to be transported from the user's location to the analysis location. In some embodiments, the packaging includes pre-paid postage to simplify the process for the user. In some embodiments the packaging also includes a tamper-proof seal which shows evidence of tampering such as breakage. The tamper-proof seal may be applied, for example, to an outer portion of the package, to the collection bag, or across the seal between the closure member and the receptacle.

After a sample has been collected, the sample collection device is placed into the package or resealable packaging and transported from the user's location to the analysis location. The package can be transported in any suitable manner, for example, by postal service or by the user.

After the package arrives at the analysis location, the sample collection device is removed from the package. In one embodiment, removal of the sample collection device is achieved by slicing the package at a predetermined location such that the sample collection device is exposed but not damaged. This provides an efficient method for processing a large volume of samples, even when the package is securely sealed. Thereafter, the sample collection device is unsealed and the sample is processed. To unseal the sample collection device, in one embodiment, at least one of the closure member or the receptacle is configured to be removable at the analysis location with, for example, a specially-adapted tool. After processing, the sample may be stored in the separate sealed container or of the sample collection device may be configured to be resealable. The stored sample may be used for further testing, especially if any irregularities in the sample are detected.

I.D. Sample Collection Method

A method for collecting a sample may include at least the following steps: depositing a sample into the receptacle; sealing the closure member onto the receptacle; and releasing the fluid from within the reservoir into the receptacle.

The sample may be deposited in any practical manner. For example, if the sample is saliva, the sample may be deposited by the user spitting or drooling into the receptacle. Alternatively, the sample may be remotely collected and thereafter deposited into the receptacle.

In one embodiment, in the depositing step, the user deposits a sample into the sample tube 20 through a funnel portion 23 at the open first end 21. The sample is then collected within the body portion 25 at or near the second end of the sample tube 20. In some embodiments, the depositing step includes the user depositing a predetermined amount of saliva into the funnel portion 23; a marking on the outer surface of the body portion 25 may then be used to indicate to the user when the user has provided a sufficient amount of saliva and may cease depositing.

In another embodiment, the sample collection device includes a separate funnel 123 as shown in FIG. 6A. In this embodiment, prior to the depositing step, the funnel 123 is connected to the sample tube 120. Such a connection may simply consist of the funnel 123 being inserted into the sample tube 120 or being placed over the open end of the sample tube 120. In other embodiments, the funnel 123 may be connected to the sample tube 120 by threads. In some embodiments, the funnel 123 and the cap 110 each include threads that are compatible with threads provided on the sample tube 120. In these embodiments, if the funnel 123 is threaded to an outer diameter of the sample tube 120, the funnel 123 may include an interior liner that fits inside the opening of the sample tube 120 thereby preventing spillage during the depositing step. When a separate funnel 123 is used, the funnel 123 may be provided to the user already connected onto the sample tube 120.

To collect saliva from a user, in one embodiment, the user is instructed to wait for a period of 30-60 minutes before last eating. In some embodiments, the user will brush his/her teeth (without using toothpaste). In some embodiments, the user will rinse his/her mouth with about 50 ml of water. The user may be requested to wait for 5-10 minutes to allow the mouth to clear of water. For users able to spit, they will be instructed to spit saliva into the funnel portion 23 until saliva reaches a predetermined level within the body portion 25, such as 1 or 2 ml.

Waiting after last eating and rinsing the mouth is desirable but not essential. Collection of saliva may take several minutes. If the user finds that he/she is unable to deliver sufficient saliva, he/she may be given a few grains of table sugar or a piece of gum to chew, which may be included with the sample collection system, and told not to be concerned if some of the sugar is spit into the sample tube 20. For users unable to spit (e.g., infants, young children, individuals with limitations/disabilities), an implement (e.g., swab, transfer pipette) may be used for sample collection. Similarly, a user may be provided a liquid (e.g., mouthwash, water, saline) to gargle in his/her mouth and throat or saline to flush his/her nasal cavity. Samples collected with said liquid would be delivered into the collection vial.

The volume of sample to be collected is not particularly limited, but should be sufficient to ensure that an accurate analysis of the sample is feasible. In some embodiments, the volume of sample to be collected can be from about 1 ml to about 7 ml, 0.5 ml to 1 ml, 0.75 mL to 1.5 ml, 1 ml to 2 ml, 1.5 ml to 3 ml, 2 ml to 4 ml, 3 ml to 5 ml, 4 ml to 5 ml, 4 ml to 6 ml, or 4 ml to 7 ml.

In embodiments wherein a separate funnel 123 is used, the sample collection method includes a step of removing the funnel 123 prior to the sealing step. The removal step may be performed in any suitable manner, depending on the connection between the funnel 123 and the sample tube 120. For example, the funnel 123 may be lifted off of the sample tube 120, or when threads are used, the funnel 123 may be unthreaded from the sample tube 120.

In the sealing step, the user or clinical technician places the closure member onto the receptacle and creates a seal by, for example, applying pressure or twisting the closure member relative to the receptacle. In some embodiments, the seal may be formed by threads included on each of the closure member and the receptacle, an adhesive between the closure member and the receptacle, a latch, or other sealing mechanisms known in the art. Further, the closure member may irreversibly lock onto the receptacle in order to prevent contamination or tampering. In such embodiments, if the sample collection is tampered with, the seal between the closure member and the receptacle may show evidence of tampering, such as breakage or another indicator. Additionally, a gasket may be included at the seal on either or both of the receptacle and the closure member to ensure a tight seal and to prevent leakage. The seal may be air tight and water tight to avoid contamination of the sample and leakage of the sample.

In one embodiment shown in FIG. 1, the cap 10 includes one or more nodules 19 configured to communicate with slot 28 provided on an interior surface of the sample tube 20 at the first end 21. In such an embodiment, the cap 10 may be sealed onto sample tube 20 by aligning the nodule 19 with slot 28, and inserting nodule 19 into the slot 28. As shown in FIG. 3B, the sealing step may include threading the cap 10 onto the sample tube 20 such that the nodule 19 aligns with slot 28. Thereafter, as shown in FIG. 3C, the cap 10 is rotated relative to the sample tube 20 to create a seal. In some embodiments, the method includes twisting the cap 10 until nodule 19 reaches locking groove 29. Also, in some embodiments, slot 28 and locking groove 29 are configured to lock nodule 19 in place once nodule 19 has reached locking groove 29, for example, by allowing nodule 19 to deform into locking groove 29.

In other embodiments, the cap 10 may include threads on the inside of the cap 10 near the second cap end 12, wherein the sample tube 20 includes complimentary threads on an outer portion near the first end 20. In such embodiments, the sealing step includes threading the cap 10 onto the sample tube 20 and twisting the cap 10 to create a seal.

In one embodiment shown in FIGS. 5A-5B, the out surface of the sample tube 120 and inner surface of the cap 110 are provided with compatible threads to seal the cap 110 onto the sample tube 120. In some embodiments, the sealing step irreversibly locks the cap 110 onto the sample tube 120. Additionally, in this embodiment, the sealing step may temporally coincide with the releasing step as shown in FIG. 5A. Alternatively, the sealing step and releasing step may be separately performed. Another embodiment of the sealing step is shown in FIGS. 7B-7C, where the sample tube 220 and the cap 210 are provided with compatible threads.

In some embodiments, the sealing step provides a tactile indication notify the user that the closure member has been sealed onto the receptacle. The tactile indication may be a sound or a visual marker, such as alignment lines provided on the closure member and the receptacle. For example, as shown in FIG. 3C, once the nodule 19 has locked into the locking groove 29, an audible click sound is produced to notify the user that the cap 10 has been sealed onto sample tube 20.

In the releasing step, the sealing member is opened allowing the fluid in the reservoir to flow into the receptacle. The releasing step may be temporally separated from the sealing step, or may be simultaneous with the sealing step. The manner in which the sealing member is opened is not particularly limited. The sealing member may be, for example, a pierce-able member or a valve such as a one-way valve or a check valve.

For example, in an embodiment shown in FIG. 1, the capsule 15 includes a valve 13 near the second cap end 12, which seals outlet 40. The valve 13 may be configured to be opened, i.e., to allow communication between the interior of the capsule 15 and the interior of sample tube 20, by rotation of the cap 10 relative to the sample tube 20. In one embodiment as shown in FIG. 1, the valve 13 includes an elongated threaded member 17 and a disc 18 seated on the outlet 40. In the releasing step, as shown in FIG. 3D, the rotation of the cap 10 unseats disc 18 from the outlet 40 whereby disc 18 moves along the threaded portion 17 thereby releasing the stabilization fluid.

In another embodiment, the sealing member, such as a check valve, is opened from pressure created in the sealing step. In another embodiment, the sealing member may include two layers each including one or more openings, at least one of the layers being moveable respective of the other layer. In this embodiment, when the openings of the respective layers are not aligned, the outlet is sealed, and when the openings of the respective layers are aligned, the outlet is unsealed and flow of fluid from the reservoir is permitted through the openings of the layers. In this embodiment, the layers may be aligned by, for example, twisting the closure member after it has been sealed onto the receptacle.

In other embodiments, the releasing step may be performed by actuating a lock ring 119 provided in the cap 110, as shown in FIGS. 5A-5B. In these embodiments, threads are provided on both an inner surface of the cap 110 and an outer surface of the sample tube 120. Additionally, the lock ring 119 is configured to fit inside of the opening of the sample tube 120 and is provided with one or more channels 119a configured to allow posts 129 to run along the channels 119a. The channels 119a are angled such that, when the cap 110 is twisted onto the threads of the sample tube 120, the posts 129 move along channels 119a to apply a mechanical advantage above what the threads on the outer surface of the sample tube 120 supply. This causes the lock ring 119 to displace toward the sample tube 120, away from fluid retention disc 118 thereby releasing the fluid from the reservoir 115.

In some embodiments, as shown in FIG. 5B, prior to the cap 110 being threaded onto the sample tube 120, the lock ring 119 is locked onto the fluid retention disc 118 via the cuff-link portion 119b. After the cap 110 is threaded onto the sample tube 120, the downward forced caused by the angle of channel 119a pulls the lock ring 119 free from the fluid retention disc 118.

In the embodiment shown in FIGS. 5A-5B, the releasing step is performed during the sealing step. In other embodiments, the cap 110 may be first sealed onto the sample tube 120 and thereafter, the lock ring 119 may be displaced from the fluid retention disc 118 to release the fluid. For example, the posts 129 may be provided farther down the interior of the sample tube 120 such that the posts 129 do not enter channels 119a until after the cap 110 has been threaded and sealed onto the sample tube 120. Alternatively, the channels 119a may be configured to not displace the lock ring 119 until after the cap 110 has sealed onto the sample tube 120, that is, the channels 119a may be elongated with a shallower angle relative to the angle of the threads.

In another embodiment, the releasing step may be performed by pulling cap 110 away from sample tube 120 after the sealing step thereby unseating fluid retention disc 118 from the lock ring 119.

In another embodiment, as shown in FIGS. 7B-7C, the releasing step includes unseating disc 218 from outlet 240 by displacing the inner cap body 210b towards the outer cap body 210a and compressing the compressible member 210c. In this embodiment, the releasing step may be performed by, for example, threading the cap 210 onto the sample tube 220 wherein the first end 221 of the sample tube 220 applies force to the inner cap body 210b thereby displacing the inner cap body 210b in the direction of the outer cap body 210a. In this embodiment, since the disc 218 is in a fixed relationship with outer cap body 210a by way of stem 218, when the inner cap body 210b is displace, the disc 218 is unseated from the outlet 240 and the contents of the reservoir 215 are permitted to flow into the sample tube body 225. Alternatively, in embodiments wherein threads are not employed, for example, when the cap 210 is snap locked onto sample tube 220, the first end 221 of the sample tube 220 likewise provides force to the inner cap body 210b as explained above.

In some embodiments, the releasing step provides a tactile indication to notify the user that the releasing step has completed. Such an indication may be an audible noise, or the fluid within the reservoir may be colored to provide visual confirmation that the outlet is open. For example, in FIG. 3D, opening the outlet provides an auditory click as well as visual confirmation from the colored liquid, thereby ensuring that the fluid within the reservoir is released into the receptacle. Such features safeguard against the sample being left isolated from the fluid, wherein the sample could degrade prior to analysis.

Figure 2:
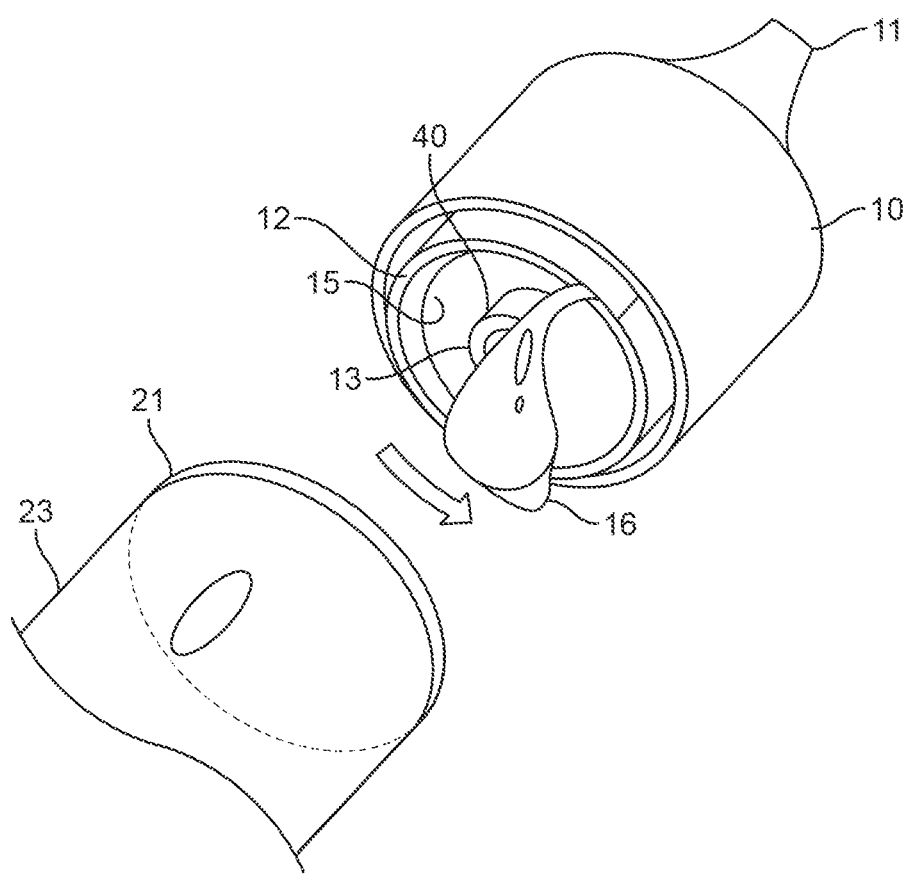
FIG. 2 is a partial perspective view of the sample collection device including a peel foil, in accordance with an embodiment.

Additionally, in some embodiments, the closure member includes a peel foil over one end of the closure member to prevent contamination. In such embodiments, the method includes an additional peeling step which may occur before or after the depositing step, but before the sealing step. An embodiment of the peeling step is depicted in FIGS. 2 and 3A. In the peeling step, peel foil 16 is removed from the closure member, cap 10. In some embodiments the peel foil 16 is provided with a pull tab or perforation to allow easy and complete removal of the peel foil 16.

The method may include additional steps. For example, after the releasing step, the method may include a shaking step wherein the user shakes the sealed sample collection device to facilitate complete release of the fluid and complete mixture of the sample and the fluid. In another embodiment, the method includes an outlet closing step after the releasing step wherein the sealing member is returned to the closed position such that mixed sample and fluid are not permitted to flow into the reservoir. This allows for easier processing since the entire mixed sample is contained in the receptacle rather than dispersed between the receptacle and the reservoir. The outlet closing step may include, for example, twisting the closure member in an opposite direction from that used in the releasing step.

Advantages of this sample collection I device, system, and method of using the same are numerous. The device can be used without clinician supervision. The design results in an easy-to-use method for sample collection. The presence of a funnel on the sample tube upon arrival at the user's location identifies the correct end of the sample tube for receiving the sample. The base on one end of the tube stabilizes the sample tube when placed on a flat surface. Closing the tube with the cap and releasing the stabilization fluid are performed with simple motions. The valve ensures that the capsule is opened once the cap is screwed onto the tube, and allows the stabilization fluid in the capsule to mix with the sample in the tube.

II. Sample Collection II

II.A. Sample Collection Device

Figure 8:
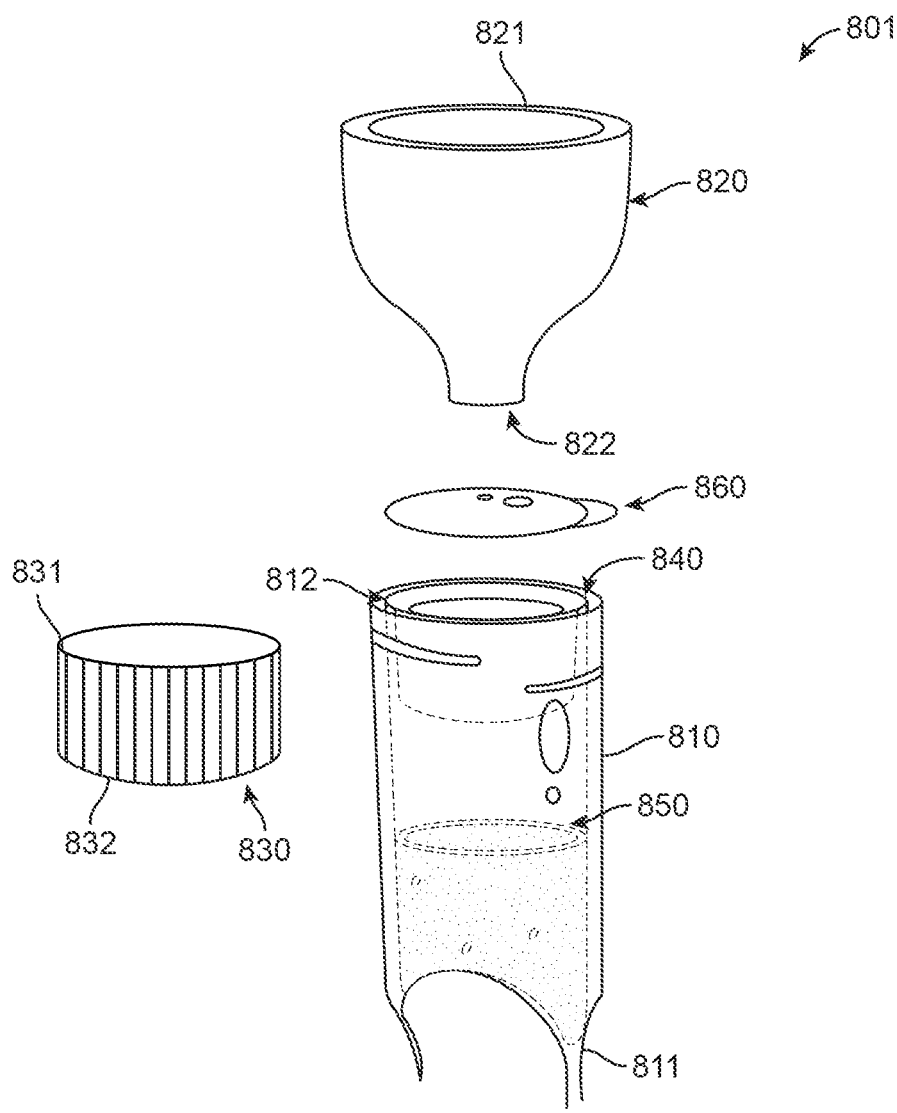
FIG. 8 is a partial perspective view of the sample collection device, in accordance with an embodiment.
Figure 9D:
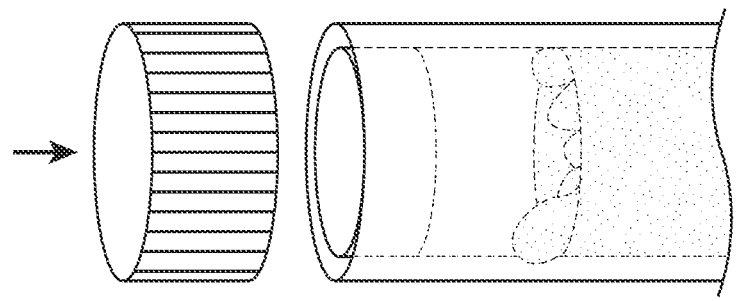
FIGS. 9A-9D are a schematic demonstration of one method of operation for the sample collection method.
Figure 9C:
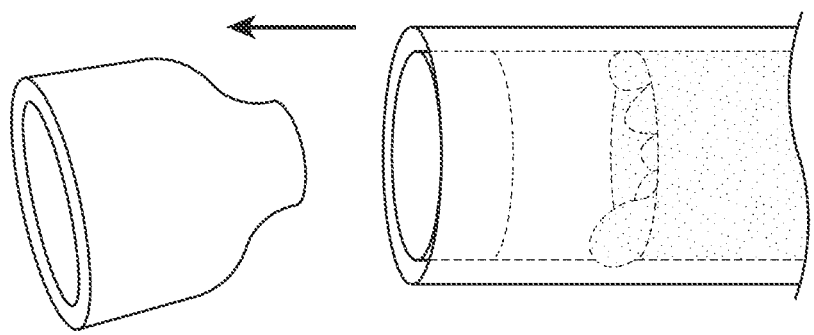
Figure 9B:
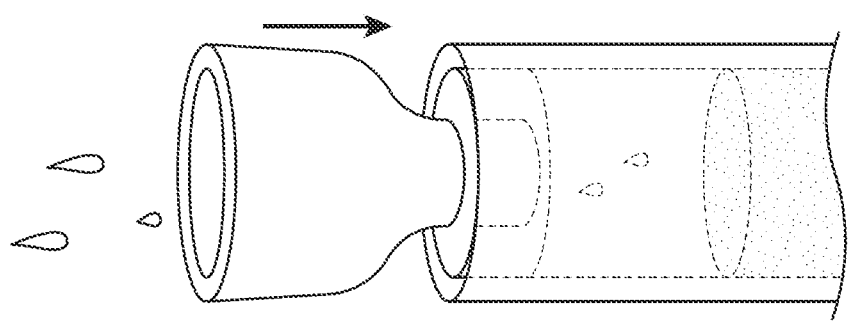
Figure 9A:
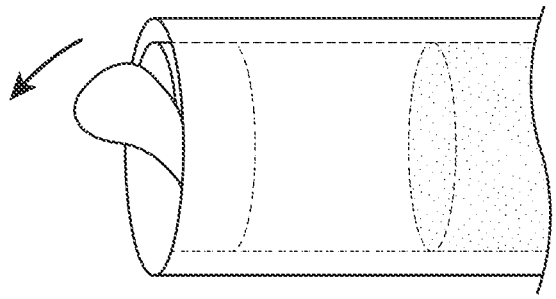

Referring to FIG. 8, a sample collection device 801 includes a sample receptacle 810, for example, a tube; a receiving member 820, for example, a funnel; an inlet which may be closed by a valve member 840, and a closure member 830, for example, a cap. The sample collection device 801 may also include a base 870 for holding the sample receptacle 810 so that the sample receptacle 810 can stand upright. The sample receptacle 810 has a closed end 811 and an open end 812. The valve member 840 is coupled to the inside of the sample receptacle near the open end 812. The sample receptacle 810 may contain a stabilization fluid 850 between the closed end 811 and the valve member 840 and may be sealed with a peelable foil 860 at the open end 812 prior to collecting the sample. The valve member 840 may be a one-way valve and may open only towards the stabilization fluid 850.

The shape of the sample receptacle 810 is not limited to that shown and may be substantially cylindrical, conical, or prismatic. The sample receptacle 810 can be a variety of shapes, as determined by the needs or preferences of the user and/or application of use, and can be specifically manufactured for use or can be a commercially available receptacle. The diameter of the sample receptacle 810 is not particularly limited and may be uniform or variable along the axial direction of the sample receptacle 810. The material of the sample receptacle 810 depends on a number of factors including manufacturing constraints and chemical suitability. In one specific embodiment, the sample receptacle 810 may be made from glass, rubber latex, silicon latex, plastics such as polypropylene, medium-density polyethylene (MDPE), high-density polyethylene (HDPE), polyethylene, or other suitable materials. The sample receptacle 810 may be a tube, a vial, or other structure that can hold the sample.

Further, the sample receptacle 810 may be marked on an inner or outer surface thereof with one or more lines representing, for example, a threshold volume of the sample to be collected or a volume of the contents of the sample receptacle 810. In the case of a saliva sample, the threshold volume line may be set at, for example, one or more of 0.5 ml, 0.75 ml, 1 ml, 1.5 ml, 2 ml, 3 ml, 4 ml, 5 ml, 6 ml, 7 ml or 10 ml. The sample receptacle may have a part that is suitable for labelling and/or for providing friction for gripping by a user.

The sample receptacle 810 may have an extended flat part on the closed end. The extended flat part may have a barcode on it for easy identification and tracking.

The closed end of the sample receptacle 810 may be configured to sit in the base 870 so that the sample receptacle 810 can stand upright.

The receptacle design provides ease of handling, and space for identification, e.g., labels and barcodes. The collection portion reduces maximum sample size and increases efficiency of mixing of the sample and stabilization fluid.

The open end of the sample receptacle 810 may also be configured for securing attachment with a closure member 830. The closure member 830 can be secured by a threaded screw, snap-fit, or other suitable configurations. Particularly, the threaded screw may include a thread with locking features.

The sample receiving member 820 may include a larger first end 821 for receiving the sample, for example, via expectorating by the user, and a smaller second end 822 which can be inserted into the valve 840 upon collection of the sample. In one embodiment, the sample receiving member is not connected to the sample receptacle. The sample receiving member 820 may be, for example, a conical funnel. The sample receiving member 820 may be tapered, with a diameter or width thereof increasing from the second end 822 toward the first end 821. The tapering may be to a degree to facilitate collecting from the user without inhibiting movement of a sample from the first end 821 to the second end 822 of the sample receiving member 820. For example, assuming the sample is a viscous liquid such as saliva, a wall of the sample receiving member 820 may be disposed at an angle of no more than 860° relative to the axial direction of the sample receiving member 820, or no more than 45°, or no more than 35°. The sample receiving member 820 may be configured to allow a user to easily deposit a sample into the sample receptacle 810. As such, in one embodiment, the sample receiving member 820 has a diameter at the first end 821 large enough to accommodate depositing a sample, for example, saliva from a user's mouth. For example, the diameter of the sample receiving member 820 at the first end 821 may be in the range from 10 to 50 mm, or 15 to 40 mm, or 20 to 30 mm. The second end 822 of the sample receiving member 820 is configured to be able to be inserted into the valve 840. Additionally, the shape of the sample receiving member 820 is not particularly limited and may be substantially cylindrical, or conical or prismatic. The sample receiving member 820 may also include a lip at the first end 821 configured to, for example, facilitate collection of the sample, avoid spillage of the sample during collection, and provide added comfort to the user.

The valve 840 is assembled into the sample receptacle 810 near the open end 812. The valve 840 allows insertion of the sample receiving member 820 upon collection of the sample and is adapted to re-seal after withdrawal of the sample receiving member 820 (that is, it resiliently recloses itself when the sample receiving member is withdrawn). The valve 840 may be an elastomeric self-resealable valve adapted to allow insertion of the smaller second end of the sample receiving member. In one embodiment, the valve 840 may be a duckbill valve, which can be stretched to allow insertion of the smaller second end of the sample receiving member from the outside. The valve 840 may be made of a resilient material that allows a slotted opening to open and close in response the insertion or withdrawal of the receiving member. The opening of the valve might be in crisscross shape.

The valve 840 may have a valve base which is attached to the inside wall of the sample receptacle. The valve base includes an aperture that is smaller in diameter than the movable flap disk which is a thin, flexible plastic disc that is large enough in diameter to completely cover the valve base aperture in the closed position. The flap disk can be permanently affixed to the base with a hinge and a tab. The flap disk can be moved by insertion of the receiving member.

In other embodiments, valve 840 may be a one-way valve including an axially-extending valve seat and an axially extending flexible valve cover which is seated on the valve seat and defines a normally closed, axially-extending seam between the valve cover and valve seat forming a fluid-tight seal therebetween. The flexible valve cover is movable relative to the valve seat, and the seam is connectable with the sample receiving member to allow passage of the sample.

The shape and size of the valve 840 is not particularly limited and is adapted to the shape and size of the sample receptacle 810.

The sample receptacle 810 may include a stabilization fluid for stabilizing the sample, for example, a sample containing nucleic acids such as DNA, during transport and storage. In o some embodiments, the sample receptacle may hold 0.25 ml to 2 ml of stabilization fluid, or 0.1 to 5 ml, or 0.5 to 3 ml, or 0.5 to 1.5 ml, or 0.5 to 1.0 ml, or about 0.75 ml of stabilization fluid. In some embodiments, the stabilization fluid includes an alcohol, at least one detergent, and at least one salt. Further, a buffer may be included in the stabilization fluid in order to maintain a constant pH. In one embodiment, the stabilization fluid includes the Formula 1 of DNA preserving solution referenced in I.B. Stabilization Fluid.

The sample receptacle 810 is sealed with a peelable member 860 at the open end 812 prior to collecting the sample. The peelable member 860 may be manufactured from, for example, a metallic foil such as an aluminum lidding foil. The peelable member can be 15-50 micrometers thick, or 20-45 micrometers, or 25-40 micrometers. The peelable member can include a heat seal lacquer material for pharmaceutical applications requiring a welded seal to polypropylene. Examples of materials for the seal include TEKNILID 81254 product and TEKNILID 81256 product (TEKNIPLEX, Tekini-Films USA, Somerville, NJ). Properties of the seal include resistance to breakage during manufacture and transport to the user and before peeling. Also, the seal may be provided with the ability to withstand corrosion by the stabilization fluid in case the valve 840 prematurely opens. Further, the peelable member 860 may include a mechanism for easy removal by the user. The mechanism can include, for example, a pull tab or weakened portion to provide easy removal by the user. The peelable member may be attached to the sample receptacle by use of adhesive, heat-sealing treatment, fasteners, or any combination thereof.

The closure member 830 includes a closed first end 831 and an open second end 832. The second end 832 is configured to connect to the open end of the sample receptacle 810, for example, via threads on the inside of the closure member 830 near the second end 832, or a spring, or a clip, or snap fit. The closure member 830 may be any suitable closure mechanism. In one embodiment, the closure member 830 may be a cap. In one embodiment, an inner diameter of the closure member 830 at the second end 832 is greater than an outer diameter of the open end 812 of the sample tube 810, such that the closure member 830 can overlap the sample receptacle 810. An inner diameter of the closure member 830 at the second end 832 may be smaller than an outer diameter of the open end 812 of the sample tube 810, such that the closure member 830 can fit inside the sample receptacle 810. The inside of the closure member 830 near the second end 832 may include a gasket to aid in sealing the closure member 830 to the sample receptacle 810. The gasket may be formed from elastomeric material, such as rubber. Additionally, the closure member 830 may be configured to lock onto the sample receptacle 810 preventing the user or unauthorized third party from tampering with the collected sample. The closure member may seal the sample receptacle in any suitable manner, such as by threads included on each of the closure member and the receptacle, an adhesive between the closure member and the receptacle, a latch, or other sealing mechanisms known in the art. In one embodiment, the closure member 830 is configured to be easily gripped by a user, for example, the first end 831 may be elongated or the surface of the closure member 830 may be textured with ridges or provided with a rubber grip portion. The closure member can be attached to the sample receptacle and tightened to seal it securely.

The sample collection device is delivered to the user without the sample receiving member connected to the sample receptacle.

II.B. Sample Collection Method

Referring to FIGS. 9A-9D a method for collecting a sample may include at least the following steps: (1) Peeling the peelable member 860 from the sample receptacle 810; (2) Inserting the receiving member 820 into the valve 840 and collecting the sample; (3) Removing the receiving member 820; and (4) Closing the sample receptacle 810 with the closure member 830.

The sample may be deposited in any practical manner. For example, if the sample is saliva, the sample may be deposited by the user spitting or drooling into the receptacle. Alternatively, the sample may be remotely collected and thereafter deposited into the receptacle.

In one embodiment, in the peeling step, the peelable member 860 is removed from the open end 812, thereby exposing the valve 840.

In the inserting and collecting step, the smaller second end 822 of the receiving member 820 is inserted into the valve 840, thus opening the valve towards the stabilization fluid 850. Then, the user deposits a sample into the sample receptacle 810 through the sample receiving member 820 at the larger first end 821. The sample is then collected into the stabilization fluid 850. In one embodiment, the collection step includes the user depositing a predetermined amount of saliva into the sample receptacle 810; a marking on the outer surface of the sample receptacle 810 may then be used to indicate to the user when the user has provided a sufficient amount of saliva and may cease depositing.

To collect saliva from a user, in one embodiment, the user is instructed to wait for a period of 30-60 minutes before last eating. In some embodiments, the user will brush his/her teeth (without using toothpaste). In some embodiments, the user will rinse his/her mouth with about 50 ml of water. The user may be requested to wait for 5-10 minutes to allow the mouth to clear of water. While waiting, the user can leave the sample vessel on the base. For users able to spit, they will be instructed to spit saliva into the receiving member 820 until saliva reaches a predetermined level within the sample receptacle 810, such as 1 to 2 ml. Waiting after last eating and rinsing the mouth is desirable but not essential. Collection of saliva may take several minutes. If the user finds that he/she is unable to deliver sufficient saliva, he/she may be given a few grains of table sugar to chew, and told not to be concerned if some of the sugar is spit into the sample receptacle 810. For users unable to spit (e.g., infants, young children, individuals with limitations/disabilities), an implement (e.g., swab, transfer pipette) may be used for sample collection. Similarly, a user may be provided a liquid (e.g., mouthwash, water, and saline) to gargle his/her mouth and throat or saline to flush his/her nasal cavity. Samples collected with said liquid would be delivered into the sample receptacle.

In the removing step, after a pre-determined amount of saliva is collected, the sample receiving member is removed and the valve closes upon removal of the sample receiving member.

In the closing step, the closure member 830 is threaded onto or snap fit onto, the sample receptacle 810, or by other mechanism, and thus tightly closes the sample receptacle. The saliva is then mixed with the stabilization fluid by shaking the sample receptacle.

II.C. Sample Collection System

Also provided is a sample collection system. The sample collection system includes a packaging containing the sample collection device with instructions for collecting, stabilizing, preserving and/or transporting the sample.

The sample collection device 801 may be supplied to a user by way of postal services or at a retail location. Alternatively, the sample collection device 801 may be administered clinically. In one embodiment, upon arrival to a user, the sample collection device 801 is contained within a packaging; the packaging may include instructions for use of the sample collection device 801. The instructions may vary depending on whether the sample is to be collected at a clinic or in-home by the user. Additionally, the instructions may direct the user to activate an online account and/or enter personal information to ensure accurate processing. Further, the packaging may include a sealable package for transporting the collected sample from the user's location to the analysis location. Alternatively, the packaging may be resealable and configured to be transported from the user's location to the analysis location.

In some embodiments, after a sample has been collected, the package including the sealed sample collection device 801 is transported from the user's location to the analysis location. The package can be transported, for example, by postal service. At the analysis location, the sample collection device 801 is removed from the package by any suitable mechanism. Thereafter, the sample collection device 801 is unsealed and the sample is processed. To unseal the sample collection device 801, in one embodiment, the closure member 830 and the valve 840 are configured to be removable at the analysis location. After processing, the sample may be stored in the sample receptacle 810 or elsewhere. In some embodiments, the sample is stored in a sealed container.

Advantages of this sample collection II device, system, and method of using the same are numerous. The device has fewer parts and is easy to manufacture. The device can be used without clinician supervision. The design results in an easy-to-use method for sample collection. Removal of the receiving member and closing the receptacle with the closure member are performed with simple motions. The valve facilitates complete mixing of the stabilization fluid and the sample in the receptacle and ensures that the mixture does not flow out of the receptacle. The device is tampering proof and the instructions are easy to follow by the user.

III. Sample Collection III

III.A. Sample Collection Device

Figure 10:
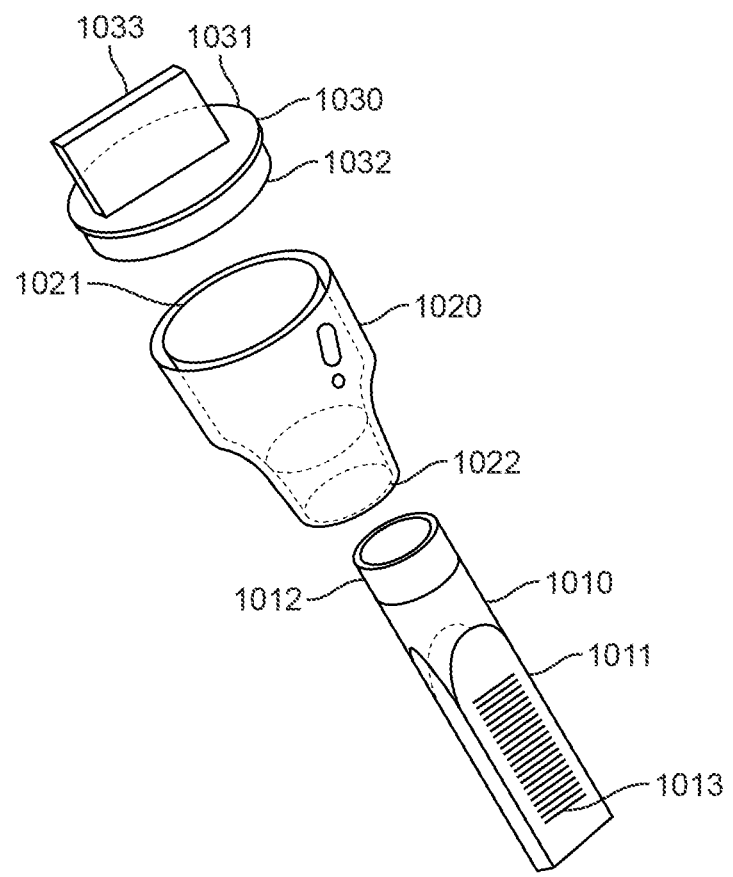
FIG. 10 is a perspective view of one embodiment of the vessel sample collection device.

Referring to FIG. 10, a sample collection device 1001 includes a sample vessel 1010, a sample receiving portion or member 1020 and a closure member 1030. The sample vessel has a closed end 1011 and an open end 1012. The closed end 1011 may include an extended flat part 1013. The sample vessel 1010 may contain a stabilization composition 1050. The sample collection device 1001 may also include a base 1040 for holding the sample vessel 1010 so that the sample vessel 1010 can stand upright.

The shape of the sample vessel 1010 is not limited to that shown and may be substantially cylindrical, conical, or prismatic. The sample vessel 1010 can be a variety of shapes, as determined by the needs or preferences of the user and/or application of use, and can be specifically manufactured for use or can be a commercially available vessel. The diameter of the sample vessel 1010 is not particularly limited and may be uniform or variable along the axial direction of the sample vessel 1010. The material of the sample vessel 1010 depends on a number of factors including manufacturing constraints, and chemical suitability. In one specific embodiment, the sample vessel 1010 may be made from glass, rubber latex, silicon latex, plastics such as polypropylene, medium-density polyethylene (MDPE), high-density polyethylene (HDPE), or polyethylene. The sample vessel 1010 may be a tube, a vial, or other structure that can hold the sample.

Further, the sample vessel 1010 may be marked on an inner or outer surface thereof with one or more lines representing, e.g., a threshold volume of the sample to be collected or a volume of the contents of the sample vessel 1010. In the case of a saliva sample, the threshold volume line may be set at, for example, one or more of 0.5 ml, 0.75 ml, 1 ml, 1.5 ml, 2 ml, 3 ml, 4 ml, 5 ml, 6 ml, 7 ml or 10 ml. The sample vessel may have a part that is suitable for labelling and/or for providing friction for gripping by a user.

The sample vessel 1010 may have an extended flat part 1013 on the closed end 1011. The extended flat part 1013 may have a barcode on it for easy identification and tracking.

The closed end of the sample vessel 1010 is configured to sit in the base 1040 so that the sample vessel 1010 can stand upright.

The vessel design provides ease of handling, and space for identification, e.g., labels and barcodes. The collection portion reduces maximum sample size and increases efficiency of mixing of the sample and stabilization composition.

The sample receiving member 1020 includes a larger first end 1021 for receiving the sample, for example, via expectorating by the user, and a smaller second end 1022 connectable to the open end of the sample vessel. The sample receiving member 1020 may be tapered, with a diameter or width thereof increasing from the second end 1022 toward the first end 1021. The tapering may be to a degree to facilitate collecting from the user without inhibiting movement of a sample from the first end 1021 to the second end 1022 of the sample receiving member 1020. For example, assuming the sample is a viscous liquid such as saliva, a wall of the sample receiving member 1020 may be disposed at an angle of no more than 60° relative to the axial direction of the funnel 20, or no more than 45°, or no more than 35°. The sample receiving member 1020 may be configured to allow a user to easily deposit a sample into the sample vessel 1010. As such, in one embodiment, the sample receiving member 1020 has a diameter at the first end 1021 large enough to accommodate depositing saliva from a user's mouth. For example, the diameter of the sample receiving member 1020 at the first end 1021 may be in the range from 10 to 100 mm, or 15 to 50 mm, or 20 to 40 mm. The second end 1022 of the sample receiving member 1020 is configured to be able to be connected to the open end 1012 of the sample vessel 1010. Additionally, the shape of the sample receiving member 1020 is not particularly limited and may be substantially cylindrical, or conical or prismatic. The sample receiving member 1020 may be, for example, a conical funnel.

In one embodiment, the sample collection device is delivered to the user with the sample receiving member connected to the sample vessel.

In another embodiment, the sample collection device is delivered to the user without the sample receiving member connected to the sample vessel, leaving up to the user to connect the two.

The sample vessel 1010 may include a stabilization composition for stabilizing the sample, for example, a sample containing nucleic acids such as DNA, during transport and storage. The stabilization composition may be a dry stabilization composition which may be in the form of powder, tablet, capsule, or other solid form, located at the bottom of the vessel, for example, in a sealed manner. The stabilization composition includes ingredients necessary to stabilize the sample and perhaps some additive(s). The stabilization composition may include a liner. For example, while the stabilization composition is a powder, the liner can function to retain the powder. The stabilization composition, and the liner if provided, dissolves upon contact with the sample. The stabilization composition can contain some ingredients that are used in same stabilization fluids for DNA samples. In some embodiments, the capsule can hold 0.25 ml to 2 ml of stabilization fluid, or 0.1 to 5 ml, or 0.5 to 3 ml, or 0.5 to 1.5 ml, or 0.5 to 1.0 ml, or about 0.75 ml of stabilization fluid. In some embodiments, the stabilization fluid includes an alcohol, at least one detergent, and at least one salt. Further, a buffer may be included in the stabilization fluid in order to maintain a constant pH. In one embodiment, the stabilization fluid includes the following Formula 1 referenced in I.B. STABILIZATION FLUID.

The sample vessel or the receiving member may be sealed with a peelable member at the open end prior to collecting the sample. The peelable member may be manufactured from, for example, a metallic foil such as an aluminum lidding foil. The peelable member can be 15-50 micrometers thick, or 20-45 micrometers, or 25-40 micrometers. The peelable member can include a heat seal lacquer material for pharmaceutical applications requiring a welded seal to polypropylene. Examples of materials for the seal include TEK-NILID 101254 product and TEKNILID 101256 product (TEKNIPLEX, Tekini-Films USA, Somerville, NJ). Properties of the seal include resistance to breakage during manufacture and transport to the user and before peeling. Also, the seal may also have the ability to withstand corrosion by the stabilization composition. Further, the peelable member may include a mechanism for easy removal by the user. The mechanism can include, for example, a pull tab or a perforated portion. The peelable member may be attached to the sample vessel or receiving member by use of adhesive, heat-sealing treatment, fasteners, or any combination thereof.

The closure member 1030 includes a closed first end 1031 and an open second end 1032. In one embodiment, the second end 1032 is configured to connect to the first end 1021 of the sample receiving member 1020, for example, via threads on the inside of the sample receiving member 1030 near the second end 1032, or a spring, or a clip, or snap fit. More particularly, the threads may include threads having locking features. In one embodiment, an inner diameter of the closure member 1030 at the second end 1032 is greater than an outer diameter of the first end 1021 of the sample receiving member 1020, i.e., such that the closure member 1030 can overlap the sample receiving member 1020. An inner diameter of the closure member 1030 at the second end 1032 may be smaller than an outer diameter of the first end 1021 of the sample receiving member 1020, such that the closure member 1030 can fit inside the sample receiving member 1020. The inside of the closure member 1030 near the second end 1032 may include a gasket to aid in sealing the closure member 1030 to the sample receiving member 1020. The gasket may be formed from elastomeric material, such as rubber. Additionally, the closure member 1030 may be configured to lock onto the sample receiving member 1020 preventing the user or unauthorized third party from tampering with the collected sample. The closure member 1030 may lock onto the sample receiving member 1020 by mechanism of, e.g., a rack and pinion configuration common to cable ties. In one embodiment, the closure member 1030 is configured to be easily gripped by a user, e.g., the first end 1031 has a projection such as a tab 1033 or the surface of the closure member 1030 may be textured with ridges or provided with a rubber grip portion. The closure member can be attached to the funnel and tightened to seal it securely.

In another embodiment, the second end 1032 of the closure member is configured to connect to the open end of the sample vessel 1010. The connecting mechanism between the closure member and the sample vessel is similar to that between the closure member and the sample receiving member. In this case, the sample collection device is delivered to the user without the sample receiving member connected to the sample vessel.

III.B. Sample Collection Method

Referring to FIG. 11, a method for collecting a sample using the vessel sample collection device may include at least the following steps: (1) Activating the device; (2) Opening the closure member and collecting the sample through the sample receiving member connected to the sample vessel; (3) Closing the sample receiving member or sample vessel using the closure member.

The sample may be deposited in any practical manner. For example, if the sample is saliva, the sample may be deposited by the user spitting or drooling into the receptacle. Alternatively, the sample may be remotely collected and thereafter deposited into the receptacle.

In one embodiment, in the activation step, the user creates an online account. The activation step may include entering personal data, and a unique identification code associated with the sample collection device and the user. The unique identification code may be marked on the sample vessel and a box. The activation step provides the benefit of providing more accurate and reliable results.

In the collecting step, the closure member 1030 is removed from the first end 1021 of the sample receiving member 1020, thereby exposing the sample receiving member 1020, then the user deposits a sample into the sample vessel 1010 through the sample receiving member 1020 at the larger first end 1021. The stabilization composition in the sample vessel dissolves upon collection of the sample. In one embodiment, the collection step includes the user depositing a predetermined amount of saliva into the sample vessel 1010; a marking on the outer surface of the sample vessel 1010 may then be used to indicate to the user when the user has provided a sufficient amount of saliva and may cease depositing.

To collect saliva from a user, in one embodiment, the user is instructed to wait for a period of 30-60 minutes before last eating. If possible, the user will brush his/her teeth (without using toothpaste). If possible, the user will rinse his/her mouth with about 50 ml of water. The user may be requested to wait for 5-10 minutes to allow the mouth to clear of water. While waiting, the user can leave the sample vessel on the base. For users able to spit, they will be instructed to spit saliva into the sample receiving member 1020 until saliva reaches a predetermined level within the sample vessel 1010, such as 1 to 2 ml. Waiting after last eating and rinsing the mouth is desirable but not essential. Collection of saliva may take several minutes. If the user finds that he/she is unable to deliver sufficient saliva, he/she will be given a few grains of table sugar to chew, and told not to be concerned if some of the sugar is spit into the sample vessel 1010. For users unable to spit (e.g., infants, young children, individuals with limitations/disabilities), an implement (e.g., swab, transfer pipette) may be used for sample collection. Similarly, a user may be provided a liquid (e.g., mouthwash, water, saline) to gargle his/her mouth and throat or saline to flush his/her nasal cavity. Samples collected with said liquid would be delivered into the collection vessel.

In the closing step, after a pre-determined amount of the sample is collected, the closure member 1030 is threaded onto or snap fit onto the sample receiving member 1020, or by other mechanism, and thus tightly closes the sample receiving member connected with the sample vessel. The sample is then mixed with the stabilization composition by shaking the vessel.

In the case of the sample collection device being delivered to the user without the sample receiving member connected to the sample vessel, the closure member would be removed from the sample vessel, then the sample receiving member is connected to the sample vessel, the sample is collected and the sample receiving member is removed after collection of the sample, and the sample vessel is closed using the closure member.

III.C. Sample Collection System

Also provided is a sample collection system. The sample collection system includes a packaging containing the sample collection device with instructions for collecting, stabilizing, preserving and/or transporting the sample.

Figure 12:
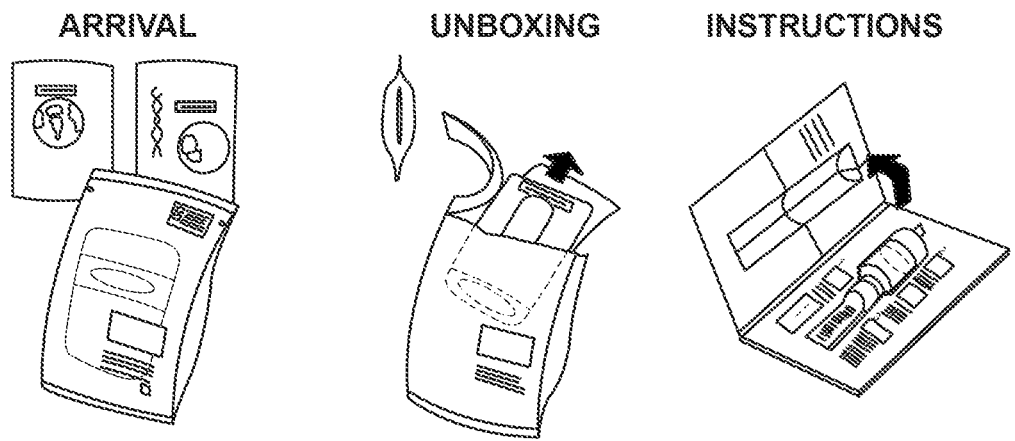
FIG. 12 is a schematic demonstrating packaging upon arrival to a user according to one embodiment.

Referring to FIG. 12, the vessel sample collection device 1001 may be supplied to a user by way of, for example, postal services or at a retail location. Alternatively, the sample collection device 1001 may be administered clinically. In one embodiment, upon arrival to a user, the sample collection device 1001 is contained within a packaging; the packaging may include instructions for use of the sample collection device 1001. The instructions may vary depending on whether the sample is to be collected at a clinic or in-home by the user. Additionally, the instructions may direct the user to activate an online account and/or enter personal information and a unique identification code on the sample vessel and package to ensure accurate processing. Further, the packaging may include a sealable package for transporting the collected sample from the user's location to the analysis location. Alternatively, the packaging may be resealable and configured to be transported from the user's location to the analysis location.

Figure 13:
FIG. 13 is a schematic demonstrating transportation of the collected sample according to one embodiment.

Referring to FIG. 13, in one embodiment, after a sample has been collected, the package including the sealed sample collection device 1001 is transported from the user's location to the analysis location. The package can be transported, e.g., by postal service.

Figure 14:
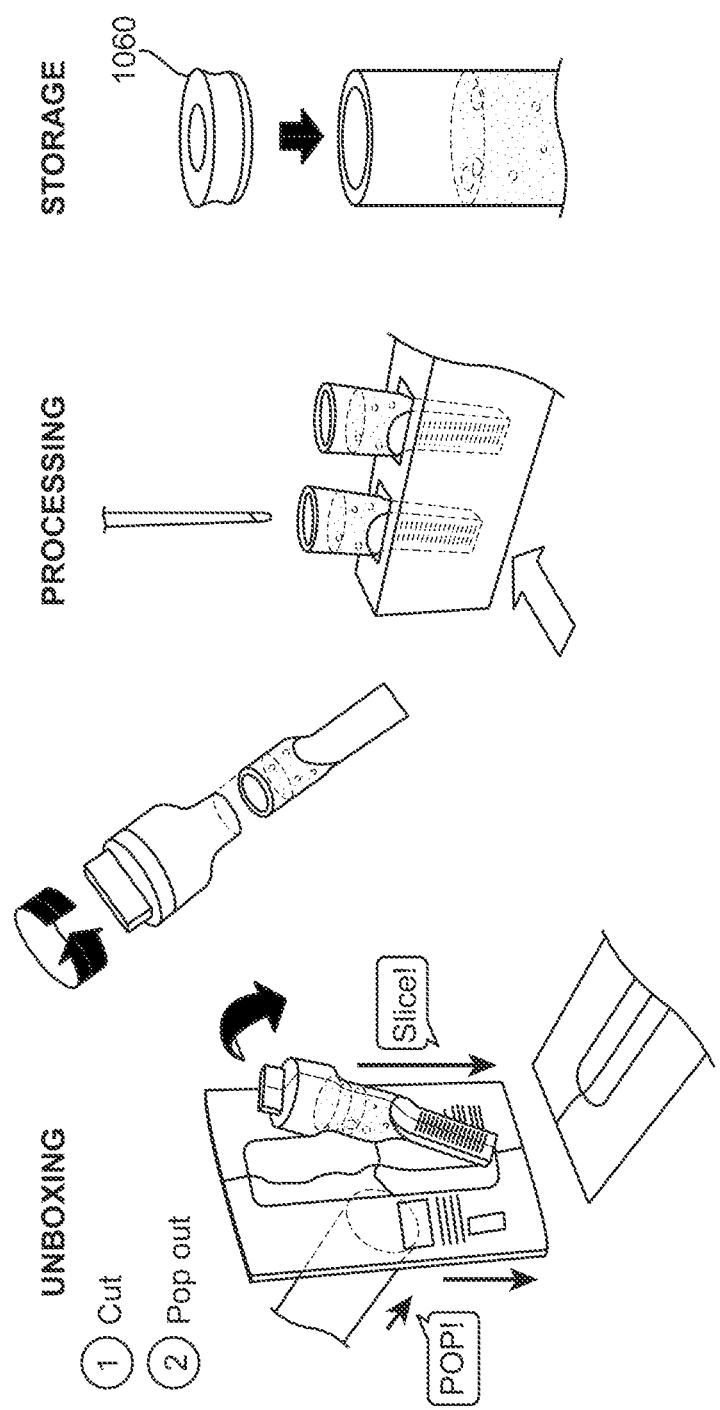
FIG. 14 is a schematic demonstrating processing and storage of the collected sample according to one embodiment.

Referring to FIG. 14, in one embodiment, at the analysis location, the sample collection device 1001 is removed from the package by any suitable mechanism. Thereafter, the sample collection device 1001 is unsealed and the sample is processed. To unseal the sample collection device 1001, in one embodiment, the sample receiving member 1020 and the closure member 1030 are configured to be removable at the analysis location. The barcode on the sample vessel 1010 is scanned and the sample is processed. After processing, the sample vessel 1010 may be sealed by a rubber stopper or other sealing mechanism 1060 and the sample may be stored in the sample vessel 1010 or elsewhere. In some embodiments, the sample is stored in a sealed container.

Advantages of this sample collection III device, system, and method of using the same are numerous. The device has fewer parts and is easy to manufacture. The device can be used without clinician supervision. The design results in an easy-to-use method for sample collection. Removal of the sample receiving member and closing the vessel with the closure member are performed with simple motions. The device is tampering proof and the instructions are easy to follow by the user.

IV. Sample Collection IV

IV.A. Sample Collection Device

The sample collection device includes a sampling member for collecting a sample. The sampling member is not particularly limited in shape or form. In some embodiments, the sampling member includes a spherical member such as a sampling pop, hereinafter referred to as a pop or sampling pop. The material forming the sampling member is not particularly limited and may include an absorbent material. Additionally, the sampling member may include a coating on its outer surface, such as a flavor layer configured to dissolve during collection of a sample. In cases where the sample to be collected is saliva, the flavor layer may increase salivation and may be used to indicate when collection is complete. In other embodiments, the surface of the sampling member is textured in order to increase the sampling surface area to collection more sample.

The sampling member is connected to a base. In some embodiments, the sample collection device includes a stem between the pop and the base. Additionally, the sample collection device includes a closure member configured to connect to the base and seal the sampling member within the closure member. The base includes a reservoir configured to contain a liquid which is releasable after the closure member has been sealed onto the base. For example, the reservoir may include an openable vent configured to release the fluid. In other embodiments, the reservoir may be breakable in order to release the fluid to be mixed with the sampling member. In some embodiments, the reservoir is a hidden reservoir, which provides a more aesthetically pleasing sample collection device.

Figure 15:
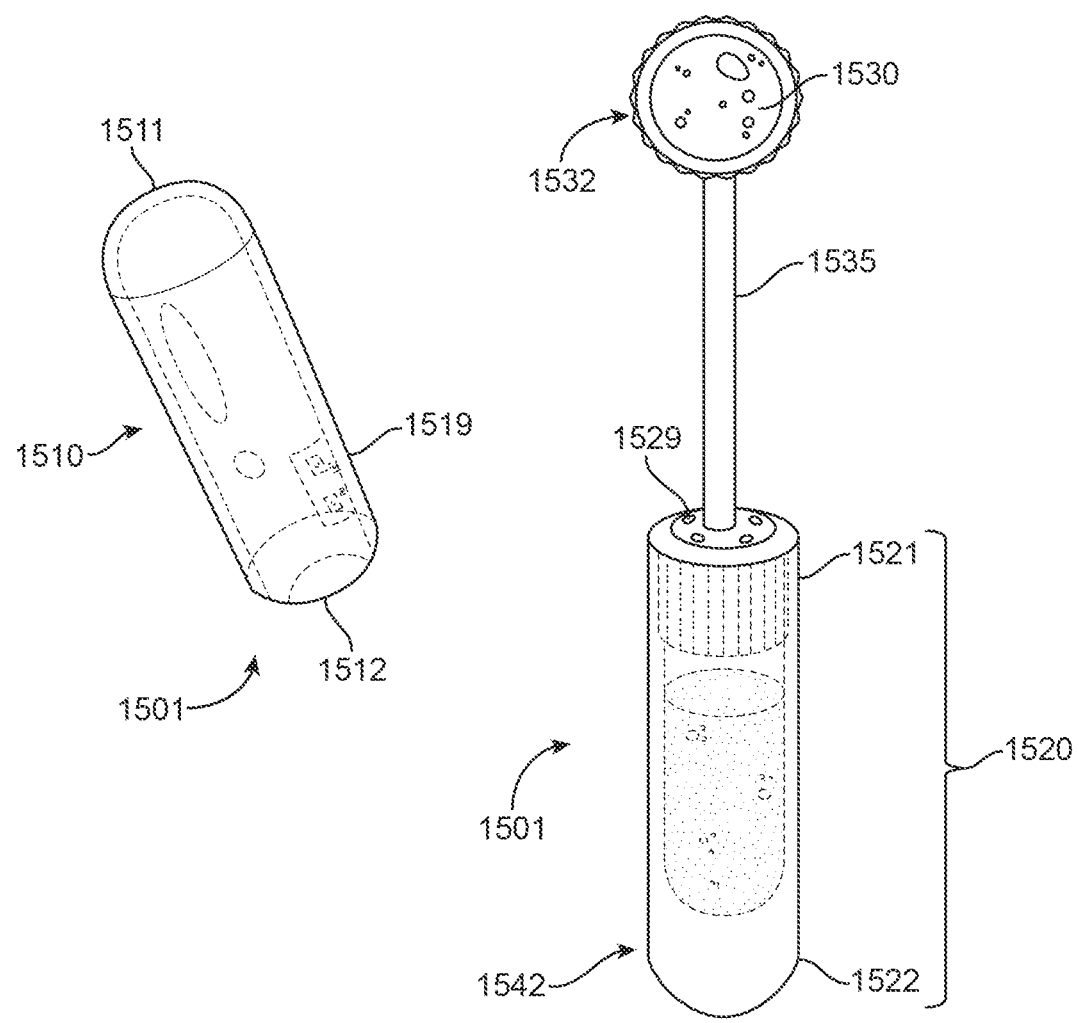
FIG. 15 is a perspective view of one embodiment of the sample collection device.

Referring to FIG. 15, in some embodiments, the pop sample collection device 1501 includes a sampling member which is a spherical sampling pop 1530, the sampling pop 1530 is connected to a base 1520 by way of a stem 1535. In some embodiments, the closure member is a cap 1510.

The base 1520 includes a first end 1521 and a closed second end 1522. The shape of the base 1520 is not particularly limited and may be substantially cylindrical, conical, or prismatic. Additionally, the diameter of the base 1520 is not particularly limited. The first end 1521 of the base 1520 is configured to allow connection of the base 1520 with the cap 1510. In one embodiment, the second end 1522 is a substantially flat surface, allowing the base 1520 to stand upright. In another embodiment, the diameter of the base 1520 increases approaching the second end 1522 thereby forming a flared, enlarged foundation to stably support the base 1520. In yet another embodiment, the second end 1522 includes a stabilization portion, either as an integral part thereof or affixed thereto, providing a stable foundation for the base 1520. When a separate stabilization portion is used, the stabilization portion is configured to maintain base 1520 in an upright position. The stabilization portion may be formed of any suitable material, such as rubber or plastic. In some embodiments, the stabilization portion is permanently attached to the base 1520 in a suitable manner, such as by an adhesive or a weld. In other embodiments, the stabilization portion may be detachable. For example, the stabilization portion may reversibly screw onto the base 1520 or the stabilization portion may include an interior depression into which the base 1520 is placed. In some embodiments, the stabilization portion has a flared shaped with an enlarged, flat bottom. In other embodiments, a stand may be integrated into a packaging for the sample collection device 1501. For example, the packaging may include a cutout portion into which the base 1520 fits.

In the embodiment shown in FIG. 15, the base 1520 includes a hidden reservoir 1542 containing a fluid 1540. The fluid 1540 may be a stabilization fluid for stabilizing biological samples subject to degradation. For example, the sample may be saliva or another sample including nucleic acids, and the stabilization fluid may preserve and stabilize the sample after collection, for instance, during transport and storage. In some embodiments, the hidden reservoir 1542 is provided with 0.1-4 ml of stabilization fluid 1540, or 0.1-7 ml, or 0.2-6 ml, or 0.4-5 ml, or 0.5-4 ml, or 0.5-3 ml, or 0.75-2.5 ml. In some embodiments, the hidden reservoir 1542 contains a sufficient volume of the stabilization fluid 1540 such that, after collection of a sample, the sampling pop 1530 is completely submerged within the cap 1510.

In some embodiments, the fluid 1540 may be used for stabilizing sample nucleic acids, for example, DNA, during transport and storage. In some embodiments, the hidden reservoir 1542 can hold 0.25 ml to 2 ml of fluid 1540, one or more of 0.5 ml, 0.75 ml, 1 ml, 1.5 ml, 2 ml, 3 ml, 4 ml, 5 ml, 6 ml, 7 ml or 10 ml of fluid 1540. In some embodiments, the fluid 1540 includes an alcohol, at least one detergent, and at least one salt. Further, a buffer may be included in the fluid 1540 in order to maintain a constant pH. In one embodiment, the stabilization fluid 1540 includes the following Formula 1 referenced in I.B.
Stabilization Fluid.

In another embodiment, the fluid 1540 includes one or more of chelating agent, a denaturing agent, and a reducing agent. Also, the fluid 1540 may contain a compound that reduces the viscous properties of mucin, thereby facilitating the extraction of nucleic acids contained in the sample. The fluid 1540 may be provided with the ability to stabilize nucleic acids, inhibit nucleases that may be present in a saliva sample, and be compatible with proteolytic enzymes and other reagents used to purify/amplify oligo- or polynucleotides.

Additionally, in the embodiment shown in FIG. 15, the base 1520 includes a vent 1529 at the first end 1521 of the base 1520. The vent 1529 is configured to allow communication between the hidden reservoir 1542 and the interior of the cap 1510. The vent 1529 may be in a closed position prior to the cap 1510 being placed onto the base 1520 to avoid premature spillage of the fluid 1540 or contamination of the fluid 1540. Thereafter, the vent 1529 may be opened, for example, by twisting the base 1520 relative to the cap 1510 or applying pressure between the cap 1510 and the base 1520.

The cap 1510 includes a closed first end 1511 and an open second end 1512. The second cap end 1512 is configured to connect to the first end 1521 of the base 1520, for example, by threads provided on the inside of the cap 1510 near the second cap end 1512 and on the outer surface of the base 1520 near the first end 1521. More specifically, the threads may be threads provided with locking features. In one embodiment, an inner diameter of the cap 1510 at the second cap end 1512 is greater than an outer diameter of the first end 1511 of the base 1520, such that the cap 1510 can overlap the base 1520. The inside of the cap 1510 near the second cap end 1512 may include a gasket to aid in sealing the cap 1510 to the base 1520. The gasket may be formed of an elastomeric material such as rubber. Additionally, the cap 1510 may be configured to irreversibly lock onto the base 1520 to ensure that the sample and fluid do not leak and to prevent tampering. In such embodiments, if the sample collection is tampered with, the seal between the closure member and the base may show evidence of tampering, such as breakage or another indicator.

In some embodiments, the cap 1510 includes a peel foil over the open second end 1512. Since the interior surface of the cap 1510 comes into contact with the sample dispersed in the fluid 1540, the peel foil prevents any possible contamination of the sample from the closure member. The foil can be 15-50 micrometers thick, for example, 20 micrometers or 25 micrometers thick. The foil can include a heat seal lacquer material for pharmaceutical applications requiring a welded seal to polypropylene. Examples of materials for the seal include TEKNILID 1254 product and TEKNILID 1256 product (TEKNIPLEX, Tekini-Films USA, Somerville, NJ). Properties of the seal include resistance to breakage during manufacture and transport to the user and before peeling. Also, the seal may have the ability to withstand corrosion caused by the fluid in case the sealing member prematurely opens. Further, the peel foil may include a pull tab or weakened portion to provide easy removal by the user.

In one embodiment, the cap 1510 is configured to be easily gripped by a user. For example, the surface of the cap 1510 may be textured with ridges or provided with a grip portion toward the second end 1512. In the embodiment shown in FIG. 15, the interior of the cap 1510 is hollow and of sufficient size to accommodate the sampling pop 1530 and the stem 1535 therein. The interior volume of the cap 1510 is not particularly limited, but may be sufficiently large to accommodate the entire volume of the stabilization fluid 1540 within the hidden reservoir 1542, the sampling pop 1530, and the stem 1535.

Additionally, the cap 1510 may include a label 1519 for easy identification during processing. The label 1519 may alternatively be located on the base 1520. The label 1519 may include a unique identifier, such as a number.

In the embodiment shown in FIG. 15, the sampling pop 1530 is supplied with a textured layer 1532 on an outer surface thereof. In such an embodiment, the sampling pop 1530 is configured to collect a saliva sample by way of a user licking or sucking on the sampling pop 1530 until a textured layer 1532 is fully removed therefrom. The textured layer 1532 may be flavored or unflavored, and may include additives to, for example, inhibit denaturing of the sample, such as nucleic acids, collected in the sampling pop 1530. In another embodiment, the user may lick or suck on the sampling pop 1530 for a predetermined period of time in order to collect the sample. The period of time may be, for example, 30 seconds or one minute, and is at least a period of time sufficient to allow the sampling pop 1530 to collect the sample. In other embodiments, the sampling member may be swabbed on a surface to collect a sample or may be submerged in a sample to be collected.

In the embodiment shown in FIG. 15, the sampling pop 1530 is connected to a first end of the stem 1535 in any practical manner, such as by an adhesive or a weld. For example, the stem 1535 may be inserted into the sampling pop 1530. In another embodiment, the stem 1535 and sampling pop 1530 are integrally formed. The stem 1535 may be made of, for example, plastic or other suitable materials. In one embodiment, at least a portion of the stem 1535 abutting the pop 1530 is made of a porous material thereby facilitating further absorption of sample. A second end of the stem 1535 is connected to the base 1520 in any practical manner, such as by an adhesive or a weld. The stem 1535 may sufficiently long to space the sampling pop 1530 from the base 1520 such that the user does not contact the base 1520 during collection of the sample. Such a configuration can provides comfort to the user in cases where saliva is sampled from the user's mouth, or can provide improved tractability when the sample is collected in other manners, such as from a surface or a liquid. For instance, the stem 1535 may be 10-100 mm in length, or 10-80 mm, or 15-70 mm, or 20-60 mm, or 25-50 mm, or 30-40 mm, or 10-30 mm.

IV.B. Sample Collection Method

A method for collecting a sample may include at least the following steps: (1) Depositing a sample onto the sampling member; (2) Sealing the closure member onto the base thereby sealing the sampling member inside of the closure member; (3) Opening the vent of the reservoir; and (4) Inverting the sample collection device to release the fluid from within the reservoir into the closure member.

The sample may be deposited in any practical manner. For example, if the sample is saliva, the sample may be deposited by the user licking or sucking on the sampling member. Alternatively, the sample may be remotely collected and thereafter deposited onto the sampling member by bringing the sampling member into contact with the sample. In another embodiment, the sampling member may be brought into contact with a surface having a sample on the surface to transfer the sample onto the sampling member.

In the embodiment shown in FIG. 16, the method includes placing the sampling pop 1530 into a user's mouth until the textured layer 1532 is removed therefrom, placing the second end 1512 of the cap 1510 over the sampling pop 1530 and onto the first end 1521 of the base 1520, twisting the cap 1510 relative to the base 1520 thereby locking the sampling pop 1530 within the interior of the cap 1510, further twisting the cap 1510 relative to the base 1520 thereby opening the vent 1529, and inverting and shaking the pop sample collection device 1501.

In the sealing step, the user or clinical technician places the closure member onto the base and creates a seal by, for example, applying pressure or twisting the closure member relative to the base. In some embodiments, the seal may be formed by threads included on each of the closure member and the base, an adhesive between the closure member and the base, a latch, or other sealing mechanisms known in the art. Further, the closure member may irreversibly lock onto the receptacle in order to prevent contamination or tampering. In such embodiments, if the sample collection is tampered with, the seal between the closure member and the base may show evidence of tampering, such as breakage or another indicator. Additionally, a gasket may be included at the seal on either or both of the base and the closure member to ensure a tight seal and to prevent leakage. The seal may be air tight and water tight to avoid contamination of the sample and leakage of the sample.

In the embodiment shown in FIG. 16, the sealing step includes twisting the cap 1510 relative to the base 1520, thereby locking the cap 1510 onto the base 1520. In some embodiments, the sealing step provides a tactile indication notify the user that the closure member has been sealed onto the receptacle. The tactile indication may be a sound or a visual marker, such as alignment lines provided on the closure member and the receptacle.

In the opening step, the vent is opened. The opening step may be temporally separated from the sealing step, or may be simultaneous with the sealing step. The manner in which the vent is opened is not particularly limited. The vent may be, for example, a pierce-able member or a valve such as a one-way valve or a check valve. Alternatively, as shown in FIG. 16, the vent 1529 may include multiple outlets that are opened by twisting the cap 1510 relative to the base 1520 after the cap 1510 has been locked and sealed onto the base 1520. In this configuration, the vent 1529 may include two layers each having one or more openings, at least one of the layers being moveable relative to the other layer. In this embodiment, when the openings of the respective layers are not aligned, the vent 1529 is sealed, and when the openings of the respective layers are aligned, the vent 1529 is unsealed and flow of fluid 1540 from the reservoir 1542 is permitted through the openings of the layers of the vent 1529. In this embodiment, the layers may be aligned by, for example, twisting the cap 1510 after it has been sealed onto the receptacle.

In the inverting step, the sample collection device is inverted thereby releasing the fluid from the reservoir into the closure member through the opened vent. In the inverting step, the fluid comes into contact with the sample, and may disperse the sample into the fluid in order to allow for easier processing. One embodiment is shown in FIG. 16, wherein the fluid 1540 flows through vent 1529 into the cap 1510 and the sampling pop 1530 is immersed in the fluid 1540.

The method may include additional steps. For example, as shown in FIG. 16, after the inverting step, the method may include a shaking step wherein the user shakes the sealed sample collection device to facilitate complete release of the fluid and complete mixture of the sample and the fluid. In another embodiment, the method includes a vent closing step after the inverting step wherein the vent is returned to the closed position such that mixed sample and fluid are not permitted to flow into the reservoir. This allows for easier processing since the entire mixed sample is contained in the closure member rather than dispersed between the closure member and the reservoir. The vent closing step may include, for example, twisting the closure member in an opposite direction from that used in the opening step.

Advantages of this sample collection IV device, system, and method of using the same are numerous. The device can be used without clinician supervision. The design results in an easy-to-use method for sample collection. The presence of a sampling member upon arrival at the user's location identifies the correct end of the sample collection device for receiving the sample. The sampling collection device may include a stabilization portion to stabilize the device when placed on a flat surface. Sealing the closure member onto the base and releasing the fluid are performed with simple motions. The vent ensures that the reservoir is opened once the closure member is sealed onto the tube, and allows the fluid in the reservoir to mix with the sample.

IV.C. Sample Collection System

Also provided is a sample collection system. The sample collection system includes a packaging containing the sample collection device. In some embodiments, each sample collection system includes a unique identifier, such as a number. The unique identifier matches the collected sample to the user, ensuring that analysis results are properly associated with the user. The unique identifier may be provided, for example, on one or both of the closure member and the base.

The sample collection system may be administered at a clinical location or in-home by the user, and the contents of the packaging may vary depending on the intended use. In some embodiments, the packaging includes instructions for use of the sample collection device and sample collection system. The instructions may direct the user to activate an online account and enter personal information and/or the unique identifier to ensure accurate processing. In some embodiments, the instructions guide the user or clinical technician through the collection method, including at least depositing the sample onto the sampling member, sealing the closure member over the sampling member onto the base, and opening the vent to mix the sample with the fluid contained within the reservoir.

Further, within the packaging, the sample collection device may be provided in a sealed wrapper in order to prevent contamination. The sealed wrapper may be made of any appropriate material. The closure member and base may be included in a single sealed wrapper or in two separate sealed wrappers. The sealed wrappers may include a portion, such as a perforated portion or a pull tab, to allow for easy opening by the user. The packaging may also include a collection bag in which the user places the sample collection device after collection is complete. The collection bag may be sealable to prevent contamination during transport of the sample. The packaging may include additional items, for example, in the case of collecting saliva, the packaging may include a salivation inducing member, such as piece of gum.

The packaging may include a sealable package for transporting the collected sample from the user's location to the analysis location. Alternatively, the packaging may be resealable and configured to be transported from the user's location to the analysis location. In some embodiments, the packaging includes pre-paid postage to simplify the process for the user. In some embodiments, the packaging also includes a tamper-proof seal which shows evidence of tampering such as breakage. The tamper-proof seal may be applied, for example, to an outer portion of the package, to the collection bag, or across the seal between the closure member and the receptacle.

Figure 17:
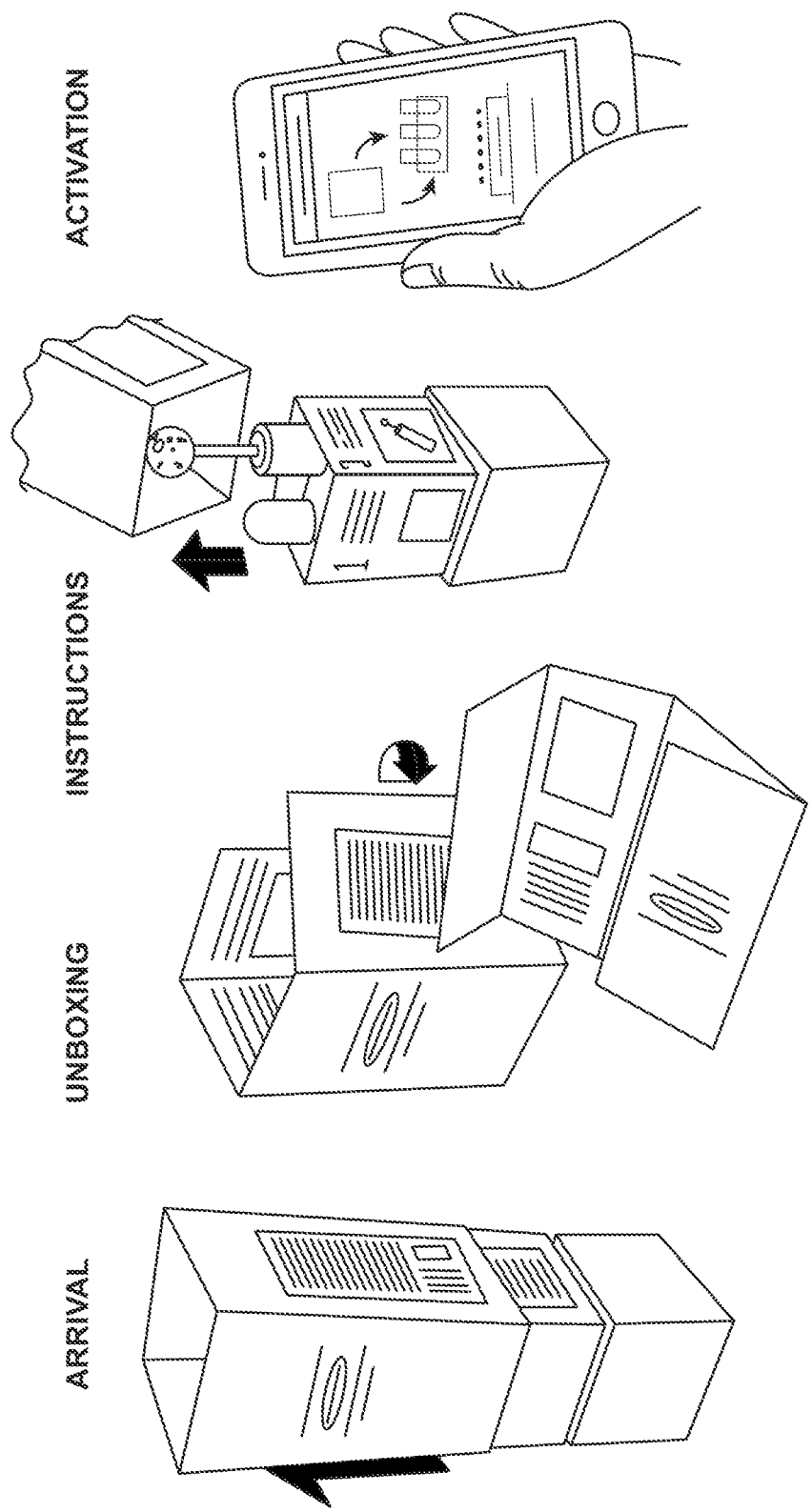
FIG. 17 is a perspective view of the packaging upon arrival to a user according to one embodiment of the sample collection system.

A sample collection system is shown in FIG. 17, wherein the sample collection system includes a packaging with a shipping label addressed to the user and a return shipping label identifying the analysis location on a return package. The system shown in FIG. 17 further includes the sample collection device and instructions for activation. As shown in FIG. 16, the return package may have a portion configured to hold the sample collection device in an upright, inverted position.

After a sample has been collected, the sample collection device is placed into the package or resealable packaging and transported from the user's location to the analysis location. The package can be transported in any suitable manner, for example, by postal service or by the user.

After the package arrives at the analysis location, the sample collection device is removed from the package. In one embodiment, removal of the sample collection device is achieved by slicing the package at a predetermined location such that the sample collection device is exposed but not damaged. This provides an efficient method for processing a large volume of samples, even when the package is securely sealed. Thereafter, the sample collection device is unsealed and the sample is processed. To unseal the sample collection device, in one embodiment, at least one of the closure member or the receptacle is configured to be removable at the analysis location with, for example, a specially-adapted tool. After processing, the sample may be stored in the separate sealed container or of the sample collection device may be configured to be resealable. The stored sample may be used for further testing, especially if any irregularities in the sample are detected.

Figure 18:
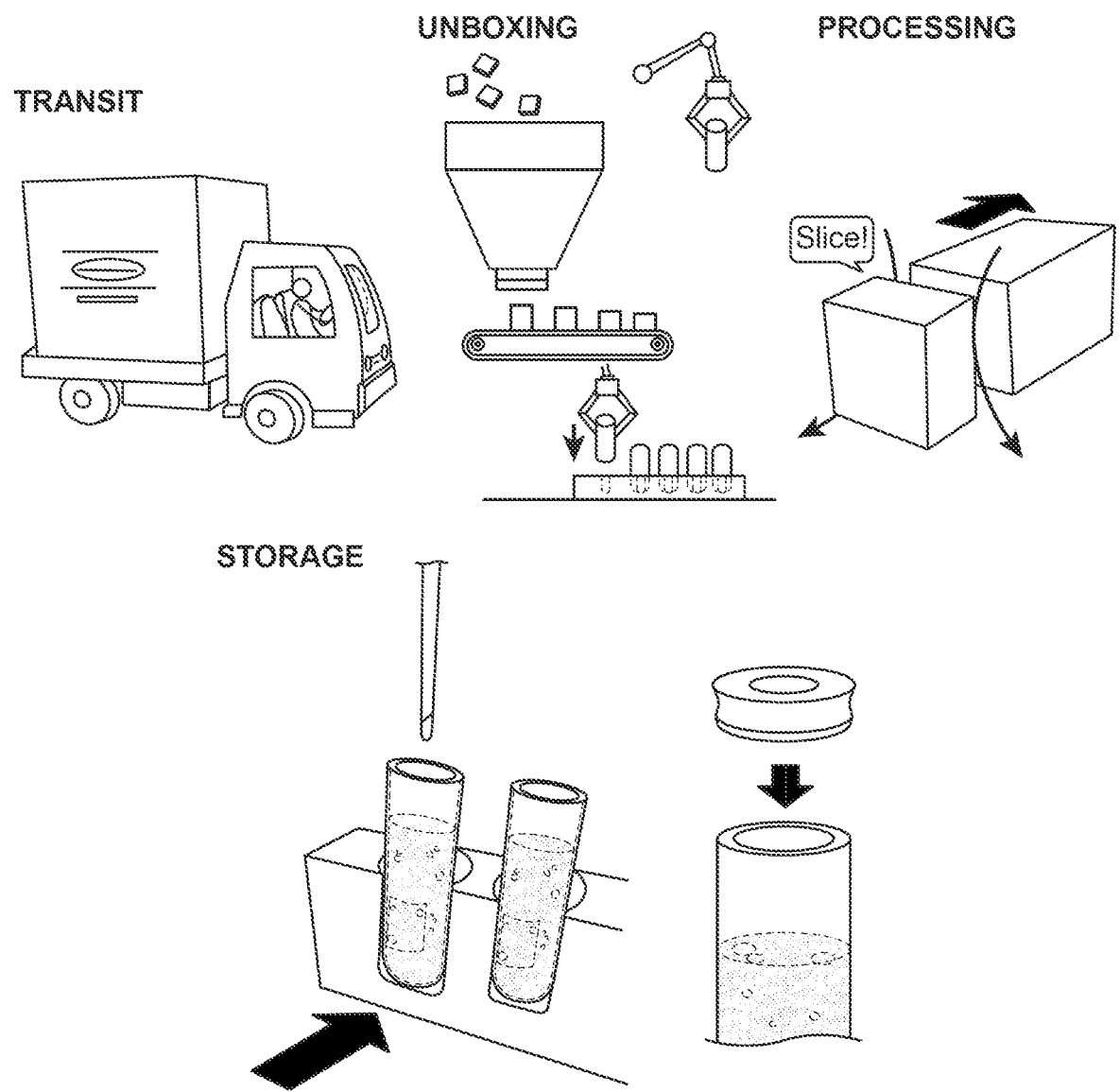
FIG. 18 is a perspective view demonstrating transportation and processing of the collected sample according to one embodiment of the sample collection system.

An embodiment of the system shown in FIG. 18 includes transit of the sample collection device contained within a return package, unboxing of the sample collection device, processing of sample, and storage of the sample. The unboxing may be performed by cutting open the return package. Additionally, the processing may include removing the base from the inverted sample collection device, for example, by using a specially-adapted tool, or cutting the sample collection device near the seal between the closure member and the base, thereby leaving the fluid and sample in the closure member. The processing further may include scanning the label of the closure member in order to accurately identify the sample. After the sample has been processed, the system may include sealing the closure member with a sealing member, such as a rubber seal.

V. Sample Collection V

V.A. Sample Collection Device

The sample collection device includes a sampling member for collecting a sample. The sampling member is not particularly limited in shape or form. Some embodiments of the sampling member include a chewing gum or spherical member such as a sampling pop. The material forming the sampling member is not particularly limited and may include gum or another absorbent material. Additionally, the sampling member may include a coating on its outer surface, such as a flavor layer configured to dissolve during collection of a sample. In cases where the sample to be collected is saliva, the flavor layer may increase salivation and may be used to indicate when collection is complete. In other embodiments, the surface of the sampling member is textured in order to increase the sampling surface area to collection more sample.

Additionally, the sample collection device includes a receptacle configured to contain a liquid and a closure member configured to connect to the receptacle and seal the sampling member within the receptacle.

Figures 19A, 19B:
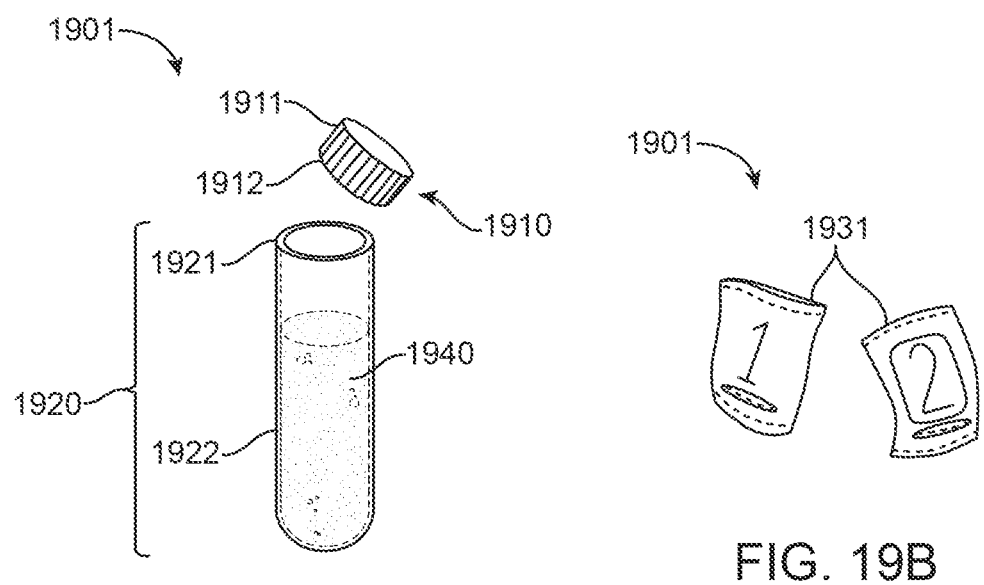
FIGS. 19A-19B are perspective views of one embodiment of the sample collection device.

Referring to FIGS. 19A-19B, in some embodiments, the sample collection device 1901 includes a sampling member being one or more pieces of sampling gum 1930, which may be contained in a wrapper 1931, a receptacle being a sample tube 1920 and closure member being a cap 1910.

The sample tube 1920 includes an open first end 1921 and a closed second end 1922. The shape of the sample tube 1920 is not particularly limited and may be substantially cylindrical, conical, or prismatic. Additionally, the diameter of the sample tube 1920 is not particularly limited and may be uniform or variable along the axial direction of the sample tube 1920. The diameter of the sample tube 1920 at the first end 1921 may be configured to facilitate connection of the sample tube 1920 with the cap 1910. In one embodiment, the second end 1922 is a substantially flat surface, allowing the sample tube 1920 to stand upright. In another embodiment, the diameter of the sample tube 1920 increases approaching the second end 1922 thereby forming a flared, enlarged foundation to stably support the sample tube 1920. In yet another embodiment, the second end 1922 includes a stabilization portion, either as an integral part thereof or affixed thereto, providing a stable foundation for the sample tube 1920. When a separate stabilization portion is used, the stabilization portion is configured to maintain sample tube

1920 in an upright position. The stabilization portion may be formed of any suitable material, such as rubber or plastic. In some embodiments, the stabilization portion is permanently attached to the sample tube 1920 in a suitable manner, such as by an adhesive or a weld. In other embodiments, the stabilization portion may be detachable. For example, the stabilization portion may reversibly screw onto the sample tube 1920 or the stabilization portion may include an interior depression into which the sample tube 1920 is placed. In some embodiments, the stabilization portion has a flared shaped with an enlarged, flat bottom. In other embodiments, a stand may be integrated into a packaging for the sample collection device 1901. For example, the packaging may include a cutout portion into which the sample tube 1920 fits.

Further, the sample tube 1920 may have an outer surface thereof marked with one or more lines or other markings representing, for example, a volume of the contents of the sample tube 1920. The sample tube 1920 may include a stabilization fluid 1940 for stabilizing the sample, which may be a sample containing nucleic acids, after collection of the sample, for example, during transport and storage. In some embodiments, the sample tube 1920 can hold 0.25 ml to 2 ml of stabilization fluid 1940, or 0.1 to 5 ml, or 0.5 to 3 ml, or 0.5 to 1.5 ml, or 0.5 to 1.0 ml, or about 0.75 ml of stabilization fluid 1940. In some embodiments, the stabilization fluid 1940 includes an alcohol, at least one detergent, and at least one salt. Further, a buffer may be included in the stabilization fluid 1940 in order to maintain a constant pH. In one embodiment, the stabilization fluid 1940 includes the following Formula 1 referenced in I.B. STABILIZATION FLUID.

In some embodiments, the sample tube 1920 contains a sufficient volume of the stabilization fluid 1940 such that, after collection of a sample, the sampling gum 1930 is completely submerged. In another embodiment, the stabilization fluid 1940 includes one or more of chelating agent, a denaturing agent, and a reducing agent. Also, the stabilization fluid 1940 may contain a compound that reduces the viscous properties of mucin, thereby facilitating the extraction of nucleic acids contained in the sample. The stabilization fluid 1940 may be provided with the ability to stabilize nucleic acids, inhibit nucleases that may be present in a saliva sample, and be compatible with proteolytic enzymes and other reagents used to purify/amplify oligo- or polynucleotides.

The cap 1910 includes a first end 1911 and a second end 1912. The second cap end 1912 is configured to connect to the first end 1921 of the sample tube 1920 in any appropriate manner, for example, by threads provided both on the inside of the cap 1910 near the second cap end 1912 and on the outside of the sample tube 1920 near the first end 1921. Alternatively, the cap 1910 may be sealed onto the sample tube 1920 by a snap-lock or an adhesive such as a tape. In one embodiment, an inner diameter of the cap 1910 at the second cap end 1912 is greater than an outer diameter of the first end 1911 of the sample tube 1920, such that the cap 1910 can overlap the sample tube 1920 to ensure a secure seal. The inside of the cap 1910 near the second cap end 1912 may include a gasket to aid in sealing the cap 1910 to the sample tube 1920. The gasket may be formed of an elastomeric material such as rubber.

Additionally, the cap 1910 may be configured to irreversibly lock onto the sample tube 1920. The cap 1910 may lock onto the sample tube 1920 in any suitable manner, for example, by a ratchet. In such embodiments, if the sample collection is tampered with, the seal between the closure member and the receptacle may show evidence of tampering, such as breakage or another indicator.

In one embodiment, the cap 1910 is configure to be easily gripped by a user, for example by a thumb and a forefinger. For instance, the surface of the cap 1910 may be textured with ridges or provided with a grip portion.

The sampling member is configured to collect a sample. For example, when the sample is saliva, the sampling member may collect the sample by a user chewing or sucking on the sampling member, such as the sampling gum 1930, for a predetermined period of time. The period of time may be, for example, 10 seconds, 15 seconds, 30 seconds, 45 seconds or one minute, and is at least a period of time sufficient to allow the sampling gum 1930 to collect the saliva sample. Alternatively, the sampling gum 1930 may be contacted with an object in order to sample the surface of the object, or the sampling gum 1930 may be submerged in a liquid to be sampled.

The sampling gum 1930 may be flavored or unflavored, and may include additives, such as additives capable of inhibiting denaturing of the sample, such as nucleic acids, collected in the sampling gum 1930. Further, the sample collection device 1901 may include one or more pieces of the sampling gum 1930. In one embodiment, two pieces of the sampling gum 1930 are provided; each piece may be separately chewed/sucked on and deposited into the sample tube 1920 or the two pieces may be combined prior to being deposited into the sample tube 1920.

Prior to use by the user, the sampling gum 1930 may be in a wrapper 1931. The wrapper 1931 may be made of any suitable material, for example, plastic. The wrapper 1931 may be configured for easy opening by the user. For example, the wrapper 1931 may include a perforated portion or a pull tab to allow easy opening.

V.B. Sample Collection Method

A method for collecting a sample may include at least the following steps: (1) Depositing a sample onto the sampling member; (2) Transferring the sampling member into the receptacle; and (3) Sealing the closure member onto the receptacle thereby sealing the sampling member inside of the receptacle.

The sample may be deposited in any practical manner. For example, if the sample is saliva, the sample may be deposited by the user licking, sucking, or chewing on the sampling member. Alternatively, the sample may be remotely collected and thereafter deposited onto the sampling member by bringing the sampling member into contact with the sample. In another embodiment, the sampling member may be brought into contact with an object having a sample on its surface to transfer the sample onto the sampling member.

Figure 20:
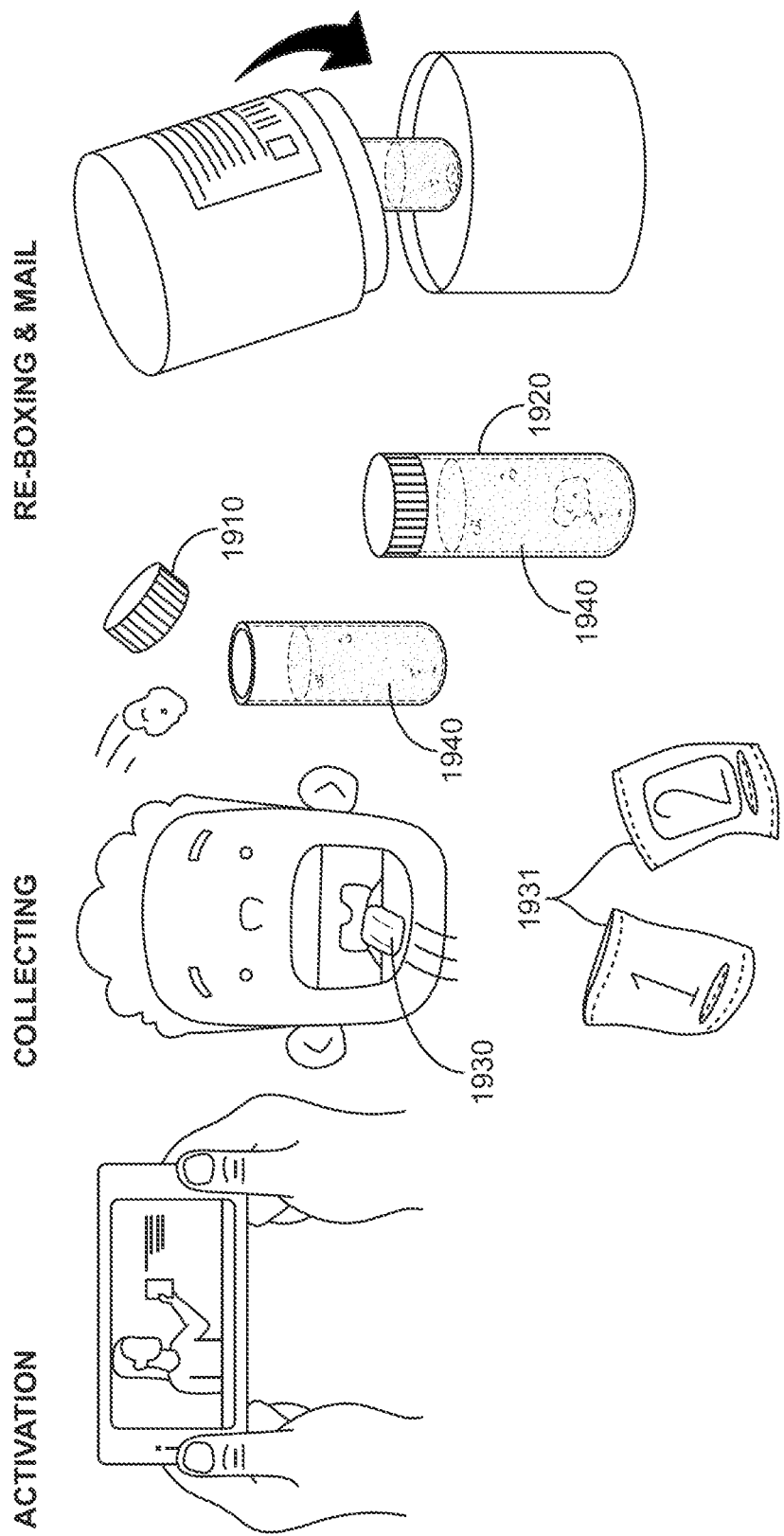
FIG. 20 is a perspective view demonstrating a collection method using the sample collection device.

In the embodiment shown in FIG. 20, the method includes placing the sampling gum 1930 into a user's mouth for a predetermined period of time, placing the sampling gum 1930 into the fluid 1940 contained in the sample tube 1920, placing the second end 1912 of the cap 1910 onto the first end 1921 of the sample tube 1920, and twisting the cap 1910 relative to the sample tube 1920 thereby locking the sampling gum 1930 within. The predetermined period of time may be, for example, 30 seconds or longer. In some embodiments, the period of time is not less than 10 seconds, or not less than 15 seconds, or not less than 25 seconds. Further, in one embodiment, the user chews the sampling gum 1930 in order to ensure that a sufficient amount of sample is passed from the user's mouth onto the sampling gum 1930.

In the transferring step, in order to avoid contamination, the sampling member may not be contacted with additional surfaces between the depositing step and the transferring step. For example, the user may spit the sampling member into the receptacle, which would have the added benefit of providing additional saliva sample. Alternatively, a user or technician may use sterile equipment, such as gloves or tongs, to transfer the sampling member from the depositing location, such as a user's mouth, to the receptacle. In some embodiments, the receptacle contains enough liquid to completely submerge the sampling member.

In the sealing step, the user or clinical technician places the closure member onto the receptacle and creates a seal by, for example, applying pressure or twisting the closure member relative to the receptacle. In some embodiments, the seal may be formed by threads, such as threads including locking features, included on each of the closure member and the receptacle, an adhesive between the closure member and the receptacle, a latch, or other sealing mechanisms known in the art. Further, the closure member may irreversibly lock onto the receptacle in order to prevent contamination or tampering. In such embodiments, if the sample collection is tampered with, the seal between the closure member and the receptacle may show evidence of tampering, such as breakage or another indicator. Additionally, a gasket may be included at the seal on either or both of the receptacle and the closure member to ensure a tight seal and to prevent leakage. The seal may be air tight and water tight to avoid contamination of the sample and leakage of the sample.

In the embodiment shown in FIG. 20, the sealing step includes twisting the cap 1910 relative to the sample tube 1920, thereby locking the cap 1910 onto the sample tube 1920. In some embodiments, the sealing step provides a tactile indication notify the user that the closure member has been sealed onto the receptacle. The tactile indication may be a sound or a visual marker, such as alignment lines provided on the closure member and the receptacle.

The method may include additional steps. For example, the method may include a shaking step wherein the user shakes the sealed sample collection device to facilitate complete mixture of the sample and the fluid.

V.C. Sample Collection System

Also provided is a sample collection system. The sample collection system includes a packaging containing the sample collection device. In some embodiments, each sample collection system includes a unique identifier, such as a number. The unique identifier matches the collected sample to the user, ensuring that analysis results are properly associated with the user. The unique identifier may be provided, for example, on one or both of the closure member and the receptacle.

The sample collection system may be administered at a clinical location or in-home by the user, and the contents of the packaging may vary depending on the intended use. In some embodiments, the packaging includes instructions for use of the sample collection device and sample collection system. The instructions may direct the user to activate an online account and enter personal information and/or the unique identifier to ensure accurate processing. In some embodiments, the instructions guide the user or clinical technician through the collection method, including at least depositing the sample onto the sampling member, placing the sampling member into the receptacle, and sealing the closure member onto the receptacle.

Further, within the packaging, the sample collection device may be provided in a sealed wrapper in order to prevent contamination. The sealed wrapper may be made of any appropriate material. The closure member and receptacle may be included in a single sealed wrapper or in two separate sealed wrappers. The sealed wrappers may include a portion, such as a perforated portion or a pull tab, to allow for easy opening by the user. Additionally, in order to avoid leakage and contamination of the fluid, the receptacle may be provided with a peel foil on the open end of the receptacle. Alternatively, in embodiments where the closure member reversibly seals onto the receptacle, the sample collection device may be provided to the user with the closure member sealed onto the receptacle.

The packaging may also include a collection bag in which the user places the sample collection device after collection is complete. The collection bag may be sealable to prevent contamination during transport of the sample. The packaging may include additional items, for example, in the case of collecting saliva, the packaging may include a salivation inducing member, such as a sugar cube.

The packaging may include a sealable package for transporting the collected sample from the user's location to the analysis location. Alternatively, the packaging may be resealable and configured to be transported from the user's location to the analysis location. In some embodiments, the packaging includes pre-paid postage to simplify the process for the user. In some embodiments, the packaging also includes a tamper-proof seal which shows evidence of tampering such as breakage. The tamper-proof seal may be applied, for example, to an outer portion of the package, to the collection bag, or across the seal between the closure member and the receptacle.

Figure 21:
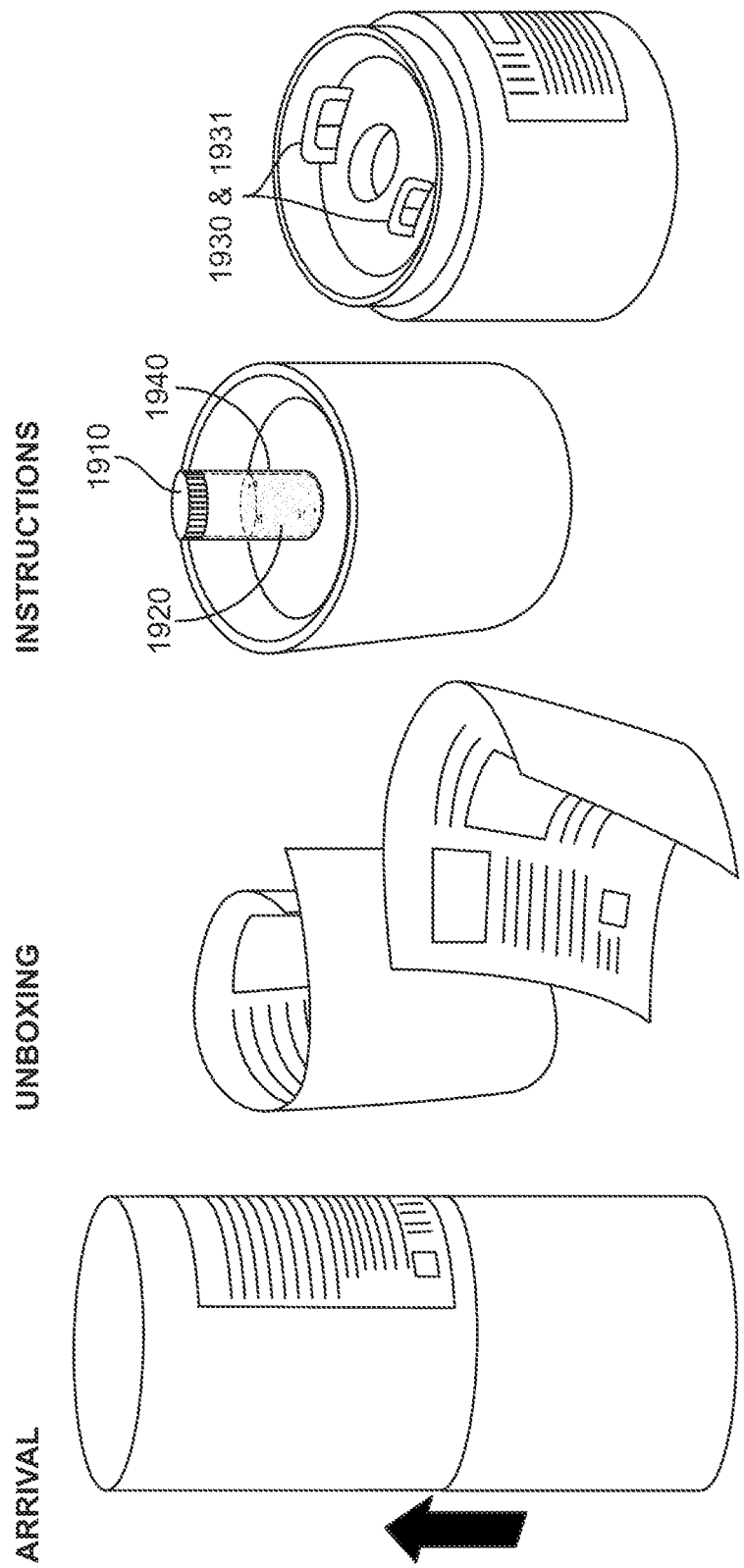
FIG. 21 is a perspective view demonstrating packaging upon arrival to a user according to an embodiment of the sample collection system.

A sample collection system is shown in FIG. 21, wherein the sample collection system includes a packaging with a shipping label addressed to the user and a return shipping label identifying the analysis location on a return package. The system shown in FIG. 21 further includes the sample collection device and instructions for activation. As shown in FIG. 20, the return package may have a portion configured to hold the sample collection device in an upright position.

After a sample has been collected, the sample collection device is placed into the package or resealable packaging and transported from the user's location to the analysis location. The package can be transported in any suitable manner, for example, by postal service or by the user.

After the package arrives at the analysis location, the sample collection device is removed from the package. In one embodiment, removal of the sample collection device is achieved by slicing the package at a predetermined location such that the sample collection device is exposed but not damaged. This provides an efficient method for processing a large volume of samples, even when the package is securely sealed. Thereafter, the sample collection device is unsealed and the sample is processed. To unseal the sample collection device, in one embodiment, at least one of the closure member or the receptacle is configured to be removable at the analysis location with, for example, a specially-adapted tool. After processing, the sample may be stored in the separate sealed container or of the sample collection device may be configured to be resealable. The stored sample may be used for further testing, especially if any irregularities in the sample are detected.

Figure 22:
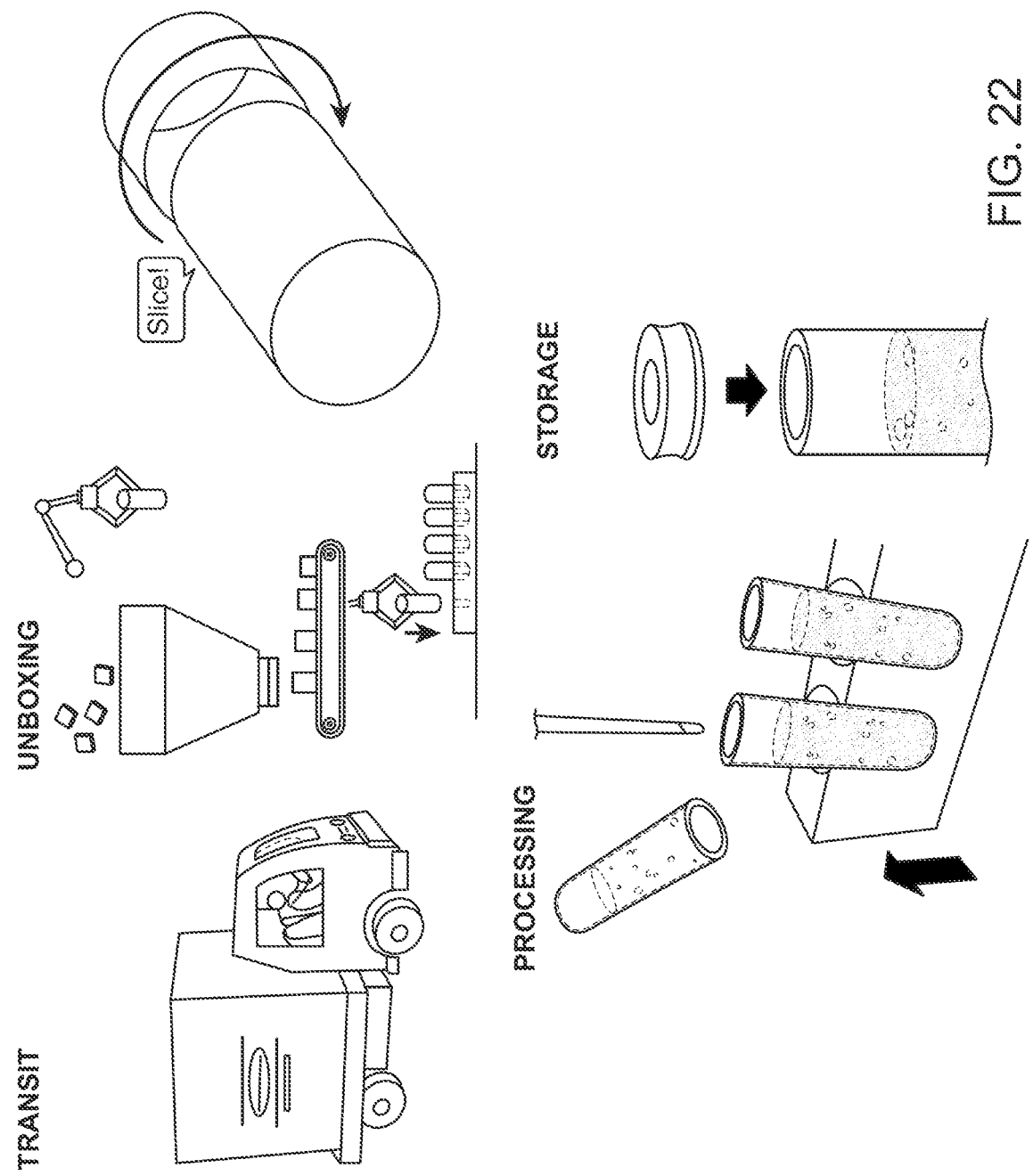
FIG. 22 is a perspective view demonstrating transportation and processing of the collected sample according to an embodiment of the sample collection system.

An embodiment of the system shown in FIG. 22 includes transit of the sample collection device contained within a return package, unboxing of the sample collection device, processing of sample, and storage of the sample. The unboxing may be performed by cutting open the return package. Additionally, the processing may include removing the closure member from the sample collection device, for example, by using a specially-adapted tool, or cutting the sample collection device near the seal between the closure member and the receptacle, thereby leaving the fluid and sample in the receptacle. The processing further may include scanning the label of the receptacle in order to accurately identify the sample. After the sample has been processed, the system may include sealing the receptacle with a sealing member, such as a rubber seal.

Advantages of this sample collection V device, system, and method of using the same are numerous. The device can be used without clinician supervision. The design results in an easy-to-use method for sample collection. The presence of an open end on the sample tube upon arrival at the user's location identifies the correct end of the sample collection device for receiving the sample. The sampling collection device may include a stabilization portion to stabilize the device when placed on a flat surface. Sealing the closure member onto the receptacle is performed with simple motions.

VI. Additional Considerations

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

While the present teachings are described in conjunction with various embodiments, it is not intended that the present teachings be limited to such embodiments. On the contrary, the present teachings encompass various alternatives, modifications, and equivalents, as will be appreciated by those of skill in the art. Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control. It must be noted that, as used in the specification and the appended claims, the singular forms "a," "an," and "the" include plural referents unless the context clearly dictates otherwise.

All references, issued patents and patent applications cited within the body of the instant specification are hereby incorporated by reference in their entirety, for all purposes.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure.

What is claimed is:

1. A DNA sample collection system, the DNA sample collection system comprising:
    a sample tube having a detachable funnel portion and a body portion, the detachable funnel portion having a first inner diameter and the body portion having a second inner diameter than is smaller than the first inner diameter, wherein the sample tube having a closed end at the body portion and an open end at the detachable funnel portion, the open end configured to receive a DNA sample;
    a reservoir-defining cap engageable with the sample tube, the reservoir-defining cap having a cap body and a sealing member movable relative to the cap body, wherein the reservoir-defining cap is lockable in place with the detachable funnel portion of the sample tube at an engaged configuration, wherein in the engaged configuration, the reservoir-defining cap closes the open end of the sample tube;
    a reservoir defined by the reservoir-defining cap, the reservoir configured to carry a stabilization fluid, the reservoir having an opening that is sealed by the sealing member of the reservoir-defining cap, wherein the sealing member is displaceable by the detachable funnel portion and relative to the reservoir to uncover the opening to release the stabilization fluid to the sample tube,
    a nodule defined by a surface of the reservoir-defining cap; and
    a slot defined in a surface of the sample tube, the slot comprising a locking groove defined at a distal terminus of the slot;
    wherein the nodule is configured to advance along a length of the slot towards the locking groove as the reservoir-defining cap is twistingly engaged with the sample tube along a longitudinal axis of the reservoir-defining cap from a disengaged configuration towards the engaged configuration;
    wherein the detachable funnel portion and the reservoir-defining cap are configured to be detached and replaced by a closure-member cap after the stabilization fluid is released to the sample tube.

2. The DNA sample collection system of claim 1, wherein the reservoir-defining cap is detachable from the sample tube.

3. The DNA sample collection system of claim 1, wherein the detachable funnel portion and the body portion of the sample tube are connected by a screw thread.

4. The DNA sample collection system of claim 1, the detachable funnel portion and the body portion of the sample tube are disengageable at a connection.

5. The DNA sample collection system of claim 4, wherein the connection includes a threaded portion, a welded portion, or an adhesive portion.

6. The DNA sample collection system of claim 1, wherein the reservoir-defining cap has a first cap end and a second cap end, and an inner diameter of the reservoir-defining cap at the second cap end is greater than an outer diameter of the first cap end.

7. The DNA sample collection system of claim 6, wherein the second cap end carries a gasket.

8. The DNA sample collection system of claim 1, wherein the sealing member comprises a valve that includes an elongated threaded member and a disc, the disc is configured to be positioned at the opening to seal the opening before the sealing member is displaced to uncover the opening.

9. The DNA sample collection system of claim 1, wherein the sample tube comprises a base member configured to allow the sample tube to be maintained in an upright position.

10. The DNA sample collection system of claim 1, wherein the locking groove is configured to lock the nodule in place when in the engaged configuration.

11. The DNA sample collection system of claim 10, wherein the nodule is configured to deform into the locking groove when in the engaged configuration.

12. The DNA sample collection system of claim 10, wherein the locking groove is configured to generate an audible sound when in the engaged configuration.

13. The DNA sample collection system of claim 8, further comprising: a compressible member situated between the cap body and the sealing member, the compressible member configured to bias the disc towards the opening in the disengaged configuration and to compress as the reservoir-defining cap is twistingly engaged with the sample tube towards the engaged configuration such that in the engaged configuration the disc is displaced from the opening of the reservoir.

14. The DNA sample collection system of claim 13, wherein the elongated threaded member is affixed to the cap body and the compressible member is a wave spring positioned above the sealing member in the engaged configuration.

* * * * *